United States Patent
Wang et al.

(10) Patent No.: US 12,313,918 B2
(45) Date of Patent: *May 27, 2025

(54) VISION CORRECTION LENS AND METHOD FOR PREPARATION OF THE SAME

(71) Applicant: EYEBRIGHT MEDICAL TECHNOLOGY (BEIJING) CO., LTD., Beijing (CN)

(72) Inventors: Zhao Wang, Beijing (CN); Jiangbing Xie, Beijing (CN)

(73) Assignee: EYEBRIGHT MEDICAL TECHNOLOGY (BEIJING) CO., LTD., Beijing (CN)

(*) Notice: Subject to any disclaimer, the term of this patent is extended or adjusted under 35 U.S.C. 154(b) by 476 days.

This patent is subject to a terminal disclaimer.

(21) Appl. No.: 17/834,139

(22) Filed: Jun. 7, 2022

(65) Prior Publication Data

US 2022/0317478 A1    Oct. 6, 2022

Related U.S. Application Data

(60) Division of application No. 16/712,377, filed on Dec. 12, 2019, now Pat. No. 11,385,479, which is a
(Continued)

(30) Foreign Application Priority Data

Jul. 24, 2015   (CN) .................... 201510440964.2
Jul. 24, 2015   (CN) .................... 201510441201.X
(Continued)

(51) Int. Cl.
*G02C 7/04*      (2006.01)
*A61B 3/10*      (2006.01)
(Continued)

(52) U.S. Cl.
CPC ............ *G02C 7/047* (2013.01); *A61B 3/1005* (2013.01); *A61F 2/1602* (2013.01); *A61F 2/164* (2015.04);
(Continued)

(58) Field of Classification Search
CPC .......... G02C 7/047; G02C 7/02; G02C 7/028; G02C 7/04; G02C 7/049; G02C 7/063;
(Continued)

(56) References Cited

U.S. PATENT DOCUMENTS 4,952,045  A    8/1990   Stoyan
5,695,509  A    12/1997  El Hage
(Continued)

FOREIGN PATENT DOCUMENTS

CN    2343997 Y    10/1999
CN    101454709    6/2009
(Continued)

OTHER PUBLICATIONS

Decision of Refusal corresponding to Japanese Application No. 2018-522844 issued Oct. 6, 2020.
(Continued)

*Primary Examiner* — Travis S Fissel
(74) *Attorney, Agent, or Firm* — Myers Bigel, P.A.

(57) ABSTRACT

The present invention discloses a method for making an aspheric vision correction lens with controlled peripheral defocus. The present invention also discloses a vision correction lens worn outside the eye, an orthokeratology lens and an intraocular lens made according to the method. The present invention further discloses a diagnosis and treatment method that utilizes myopic peripheral defocus to control and retard myopia growth.

14 Claims, 9 Drawing Sheets

Related U.S. Application Data continuation of application No. 15/746,748, filed as application No. PCT/CN2016/090955 on Jul. 22, 2016, now Pat. No. 10,551,636.

(30) Foreign Application Priority Data

| Jul. 24, 2015 | (CN) | .......................... | 201510441713.6 |
| Jul. 24, 2015 | (CN) | .......................... | 201510441714.0 |
| Jul. 24, 2015 | (CN) | .......................... | 201520543407.9 |
| Jul. 24, 2015 | (CN) | .......................... | 201520543778.7 |
| Jul. 24, 2015 | (CN) | .......................... | 201520543779.1 |

(51) Int. Cl.
*A61F 2/16* (2006.01)
*B29D 11/00* (2006.01)
*G01M 11/02* (2006.01)
*G02C 7/02* (2006.01)
*G02C 7/06* (2006.01)

(52) U.S. Cl.
CPC .. *B29D 11/00038* (2013.01); *B29D 11/00951* (2013.01); *G01M 11/0228* (2013.01); *G02C 7/02* (2013.01); *G02C 7/028* (2013.01); *G02C 7/04* (2013.01); *G02C 7/049* (2013.01); *G02C 7/063* (2013.01); *G02C 7/027* (2013.01); *G02C 2202/24* (2013.01)

(58) Field of Classification Search
CPC .... G02C 7/027; G02C 7/024; G02C 2202/24; A61B 3/1005; A61F 2/1602; A61F 2/164; A61F 2/145; A61F 2/1624; B29D 11/0038; B29D 11/00951; G01M 11/0228
USPC .................................................. 351/159.01
See application file for complete search history.

(56) References Cited

U.S. PATENT DOCUMENTS

| 5,771,088 | A | 6/1998 | Perrott |
| 7,984,988 | B2 | 7/2011 | Berke |
| 10,551,636 | B2 | 2/2020 | Wang et al. |
| 2005/0206840 | A1* | 9/2005 | Roscini ................... G02C 7/02 351/159.05 |
| 2005/0260840 | A1* | 11/2005 | Yeh ................... H01L 29/66583 257/E21.205 |
| 2007/0115431 | A1 | 5/2007 | Smith, III et al. |
| 2008/0084534 | A1 | 4/2008 | Lindacher et al. |
| 2009/0257026 | A1* | 10/2009 | Varnas ................... G02C 7/063 351/200 |
| 2009/0303442 | A1* | 12/2009 | Choo ..................... G02C 7/047 351/159.22 |
| 2011/0051079 | A1 | 3/2011 | Martinez et al. |
| 2012/0320333 | A1 | 12/2012 | Holden |
| 2015/0124212 | A1 | 5/2015 | Loertscher et al. |
| 2015/0250583 | A1 | 9/2015 | Rosen et al. |
| 2015/0320547 | A1 | 11/2015 | Rosen et al. |
| 2017/0010479 | A1 | 1/2017 | Meyers et al. |
| 2017/0296330 | A1 | 10/2017 | Rosen et al. |

FOREIGN PATENT DOCUMENTS

| CN | 102402001 | 4/2012 |
| CN | 102947748 | 2/2013 |
| CN | 203311108 U | 11/2013 |
| CN | 203745737 U | 7/2014 |
| CN | 203745738 U | 7/2014 |
| CN | 203745739 U | 7/2014 |
| CN | 204422891 U | 6/2015 |
| CN | 104749791 A | 7/2015 |
| CN | 104808353 | 7/2015 |
| CN | 204600792 U | 9/2015 |
| CN | 204964915 U | 1/2016 |
| CN | 204964916 U | 1/2016 |
| CN | 204964917 U | 1/2016 |
| CN | 106291977 | 1/2017 |
| JP | 2002303831 A | 10/2002 |
| JP | 2002350787 A | 12/2002 |
| JP | 2003514597 A | 4/2003 |
| JP | 2009525835 A | 7/2009 |
| KR | 20080100446 A | 11/2008 |

OTHER PUBLICATIONS

Notice of Preliminary Rejection corresponding to Korean Application No. 2020-057003586 issued Aug. 20, 2020.
Extended European Search Report corresponding to European Application No. 16829806.5 dated Jun. 26, 2019.
International Search Report corresponding to International Application No. PCT/CN2016/090955 mailed Oct. 25, 2016.
Office Action corresponding to Japanese Application No. 2018-522844 dated Apr. 23, 2020.
Office Action corresponding to Korean Application No. 10-2018-7005094 issued Aug. 28, 2020.
Supplementary Examination Written Opinion for Singaporean Patent Application No. 10201909653T mailed Jul. 4, 2024, 4 pages.

* cited by examiner

VISION CORRECTION LENS AND METHOD FOR PREPARATION OF THE SAME

RELATED APPLICATIONS

This application is a divisional of and claims priority to U.S. patent application Ser. No. 16/712,377 filed Dec. 12, 2019, now allowed, which is a continuation of U.S. patent application Ser. No. 15/746,748 filed Jan. 22, 2018, now U.S. Pat. No. 10,551,636, which is a 35 U.S.C. § 371 national phase application of and claims priority to PCT Application PCT/CN2016/090955 filed Jul. 22, 2016, which claims priority to Chinese Application No. 201510441714.0 filed Jul. 24, 2015, Chinese Application No. 201510440964.2 filed Jul. 24, 2015, Chinese Application No. 201510441201.X filed Jul. 24, 2015, Chinese Application No. 201510441713.6 filed Jul. 24, 2015, Chinese Application No. 201520543407.9 filed Jul. 24, 2015, Chinese Application No. 201520543778.7 filed Jul. 24, 2015, and Chinese Application No. 201520543779.1 filed Jul. 24, 2015, the entire contents of each of which is incorporated herein by reference in their entirety.

FIELD OF THE INVENTION

The present invention relates to a method for preparing a vision correction lens, and in particular to a method for preparing an aspheric vision correction lens with controllable peripheral defocus. The present invention also relates to a vision correction lens worn outside the eye, an orthokeratology lens, and an intraocular lens that are prepared according to the method. The present invention further relates to a diagnosis and treatment method that utilizes myopic peripheral defocus to control and retard myopia growth.

BACKGROUND

Defocus or out-of-focus is a word corresponding to focus. It means that the image plane is not in focus, and is divided into two states—front defocus (in front of the focus) and back defocus (behind the focus).

The main reason for increase in the degree of myopia is the increase in the axial length of the eye. For every 1 mm increase in the axial length of the human eye, myopia grows by 3.00 degrees. Recent medical studies have proved that the extension of the eyeball depends on the defocus at the periphery of the retina (as shown by 10 in FIG. 1). According to dioptric concepts, where the focus falls in front of the retina, it is called myopic defocus (as shown by 30 in FIG. 1); where the focus falls behind the retina, it is called hyperopic defocus (as shown by 20 in FIG. 1). A myopic eye exhibits myopic defocus in the center of the retina, but hyperopic defocus in the periphery of the retina. Hyperopic defocus in the periphery of the retina is the main reason for constant increase in the degree of myopia.

The eyeball has the characteristic of relying on imaging in the periphery of the retina to induce the eyeball development, especially for adolescents under the age of 18. If the peripheral retinal imaging is hyperopically out of focus, the retina tends to grow toward the image point and the eyeball length will increase. If the peripheral retinal imaging is myopically out of focus, the eyeball will stop extending. If, through modern medical methods, hyperopic defocus in the periphery of retina is corrected or myopic defocus is formed artificially in the periphery of retina, constant increase in the degree of myopia can be inhibited. Besides, the occurrence and progress of myopia can be prevented effectively by finding out the causes of defocus in the periphery of the retina.

The concept of peripheral defocus is derived from clinical practice in the field of optometry. Doctors at first found that the axial length and myopia growth of the eyes of some of the orthokeratology lens wearers was retarded, and then discovered the role of peripheral defocus in this process and formed the theory that peripheral defocus controls myopia. However, this theory has been in a state of passive discovery. The discussions among doctors and researchers in the field remain at the level of huge statistics and analysis of the peripheral defocus of the human eye, without forming an effective and quantifiable treatment implementation plan. Enterprises, research institutes and the like stay at the level of proposing some preliminary products with uncontrollable degree of peripheral defocus, such as frame glasses of a partitioned structure and optical defocus soft contact lenses, besides orthokeratology lenses which appear earlier.

The mechanism of controlling the peripheral defocus of the orthokeratology lens is to shape the anterior surface of the cornea into the shape of the inner surface of the optical zone of the orthokeratology lens (spheric surface) by wearing the lens at night, taking advantage of the activity of the cells at the surface of the cornea, and thus form of hyperopic peripheral defocus.

The disadvantage of the orthokeratology lens is that the curvature of the retina varies from one patient to another. The existing orthokeratology lens shapes the outer surface of the cornea into the spherical shape of its base curve zone, and the refractive power distribution of the outer surface of the cornea only follows the rules of refractive power distribution of the spherical surface. That is, for the same radius of curvature of the anterior surface of the shaped cornea, the refractive power distribution thereof has only a single form. When the curvature of the retina of the human eye is greater than the curvature of the refractive power distribution formed by the cornea, myopic peripheral defocus cannot be formed, and thus myopia growth cannot be controlled. Therefore, the orthokeratology lens whose base curve zone is a spherical surface cannot achieve controllable, effective peripheral refractive power control. It benefits only some of the patients and controls their myopia growth, but cannot achieve effective control of myopia of every patient.

Frame glasses have a partitioned structure. The center of the glass is designed as a precise imaging 0 spherical aberration optical zone, and the edge as a peripheral defocus control zone with a higher refractive power than the central region. The problem with this approach is that peripheral defocus exists only outside the often used optical zone, and does not work in most cases. The myopia control zone is very limited and not continuous.

As to optical defocus soft contact lenses, the lens surface structure is divided into multiple layers, which are designed to have different radians (radius of curvature). Two radians alternate to achieve hyperopic defocus of the refractive power. However, there are two problems with this way of realizing peripheral defocus control. Firstly, since the lens has only two radians, the optical imaging process is similar to that of a partitioned multifocal lens. The focuses interfere with each other and form a halo. Secondly, since the radii of curvature of the curve segments are different, joining of the rings would cause a large amount of stray light. Therefore, the biggest problem with this kind of lens is that imaging is disturbed by the multi-layer structure of the optical zone and the visual quality is poor.

So far, the technique of control myopia growth through peripheral defocus faces two major problems—a lack of a clear and quantifiable peripheral defocus control implementation plan, and a lack of an effective, controllable therapeutic product.

Therefore, there is a particular need for a method for preparing an aspheric vision correction lens with controllable peripheral defocus which can provide, according to the patient's own physiological and refractive state, a custom quantitative peripheral defocus product with a controllable degree of defocus to solve the aforesaid existing problem.

There are two types of vision correction lenses worn outside the eye—lenses in direct contact with the human eye (such as cornea contact lenses) and lenses that do not directly contact the human eye (such as frame glasses). Frame glasses are generally made of glass or resin, and have a refractive index of about 1.40 to 1.71. A cornea contact lens is one worn on the cornea of the eyeball to correct vision or protect the eye. There are three types of cornea contact lenses—rigid, semi-rigid, and soft ones, depending on the hardness of the material. The refractive index is about 1.40 to 1.50.

In the prior art, optical defocus soft contact lens is a peripheral defocus control type cornea contact lens. The surface structure of the lens is divided into multiple layers designed to have different radians (radius of curvature). Two radians alternate to realize myopic peripheral defocus of the refractive power. There are two problems with this way of realizing peripheral defocus control. Firstly, since the lens has only two radians, the optical imaging process is similar to that of a partitioned multifocal lens. The focuses interfere with each other and form a halo. Secondly, since the radii of curvature of the curve segments are different, joining of the rings would cause a large amount of stray light. Therefore, the biggest problem with this kind of lens is that imaging is disturbed by the multi-layer structure of the optical zone and the visual quality is poor.

Existing frame glasses have a partitioned structure. The center of the glass is designed as a precise imaging 0 spherical aberration optical zone, and the edge as a peripheral defocus control zone with a higher refractive power than the central region. The problem with this approach is that peripheral defocus exists only outside the often used optical zone, and does not work in most cases. The myopia control zone is very limited and not continuous.

Therefore, there is a particular need for a vision correction lens worn outside the eye to solve the aforesaid existing problem.

The design principle of "reverse geometry" is used for orthokeratology lenses. The surface (inner surface) of the entire lens contacting the cornea is designed as several curve segments joined to each other. When the lens is worn, the special shape of the inner surface of the lens causes a layer of unevenly distributed tears between the lens and the outer surface of the cornea. The hydrodynamic effect of the tears pulls the epithelial cells at the center of the cornea to the mid-peripheral portion (periphery); meanwhile, when the eye is closed, the eyelid causes the center of the lens to apply a certain pressure to the lower cornea. These two effects lead to the flattening of the curvature of the center of the cornea, and the corneal shape tends to be the shape of the base curve zone of the inner surface of the orthokeratology lens. After the lens is taken off, the refractive state of the human eye changes. The visual imaging point moves closer to the retina, thereby correcting myopia.

The "reverse geometry" design of the orthokeratology lens was proposed by Stoyan in 1989 (U.S. Pat. No. 4,952,045). The original reverse geometry design divided the orthokeratology lens into three curve zones—base curve zone, reverse curve zone and peripheral curve zone. Since the reverse curve zone of this design is very wide, the height of edge lift is large, which tends to cause irregular movement of the lens. This design has great limitations in clinical application.

Orthokeratology lenses of modern "reverse geometry" design have modified the reverse geometry zone, and are generally divided into four zones. As shown in FIG. 12, the base curve zone 11 is in contact with the central region of the cornea and is relatively flat in shape for flattening the surface of the cornea. The reverse curve zone 12 is relatively steep for reinforcing the flattening effect of the base curve zone 11 and ensuring a certain amount of tear storage. The alignment curve zone 13, also called fitting curve zone is mainly for stabilizing the lens. The peripheral curve zone 14 ensures the circulation of tears between the cornea and the periphery of the orthokeratology lens.

The inner surface of the orthokeratology lens is the region where the shaping function is realized, and most of the design is done in this region. The region is designed based on two variables—radius of curvature and width of the four curve zones, according to the patient's corneal shape and desired diopter.

At present, the design widely used in production generally has 4 to 7 or 5 to 7 curves of different radii of curvature and joined together. As shown in FIG. 12, four curve zones are the most basic design. The four curve zones take the form of four spherical surfaces with different radii of curvature, and are chamfered at the joining thereof so that the curve zones are joined naturally. 5 to 7 curves joined together means that a plurality of curves are used in the reverse curve zone 12 and alignment curve zone 13 (e.g., two curves are used in the reverse curve zone, and three curves are used in the alignment curve zone) so that the base curve zone 11 and the reverse curve zone 12 are joined more easily and the alignment curve zone 13 better fits the corneal shape (since the cornea is aspheric, a plurality of spherical surfaces are used to fit the aspheric shape). In the prior art there are also designs that use an aspheric alignment curve.

Due to the activity of corneal cells, change of the shape of the cornea brought by the orthokeratology lens is only temporary. When the patient stops wearing the orthokeratology lens, the cornea will return to its original shape. Therefore, the original orthokeratology lens is considered only as a treatment means for temporary correction of myopia. However, clinical research in subsequent years found that wearing orthokeratology lens can slow down the increase of the axial length of the human eye for some adolescents, and thus control the development of myopia. Clinical research indicates that the formation of myopic peripheral defocus after wearing the orthokeratology lens is the mechanism based on which the orthokeratology lens works.

The cornea of a normal human eye is generally aspheric, the periphery being slightly flatter than the center. After the corneal shaping, the anterior surface of the cornea becomes spherical, namely takes the shape of the posterior surface of the orthokeratology lens. FIG. 13 is a schematic diagram of the variation of the refractive power of a spherical cornea (as shown in by A in the figure) and an aspheric cornea (as shown by B in the figure) of the same radius of curvature, along with the aperture. It can be seen that compared with the aspheric cornea, the spherical cornea brings a greater refractive power to the periphery of the human eye. Therefore, the true mechanism of the orthokeratology lens controlling myopia growth is that while being worn at night, the orthokeratology lens shapes the cornea into a spherical surface (the shape of the inner surface of the optical zone of the orthokeratology lens), so that when seeing an object, the human eye has a greater refractive power in the periphery than before, enabling some wearers to form myopic peripheral defocus and thereby slowing the increase in the axial length of the human eye and controlling the development of myopia.

The base curve zones of the existing orthokeratology lenses all have a spherical surface. Spherical base curve zone will shape the anterior surface of the cornea into a spherical surface, so the refractive power distribution provided by the cornea is in line with spherical characteristics. The disadvantage is that the curvature of the retina varies from patient to patient. The existing orthokeratology lens shapes the outer surface of the cornea into the spherical shape of its base curve zone, and the refractive power distribution of the cornea only complies with the refractive power distribution rules of the spherical surface. That is, for the same radius of curvature of the anterior surface of the shaped cornea, the refractive power distribution of the cornea has only one form. For example, for a shaped cornea having a radius of curvature of 42.25D, its refractive power distribution can only be the case as shown by A in FIG. 13. When the curvature of the human eye retina is greater than the curvature of the refractive power distribution formed by the cornea as shown in the figure, myopic peripheral defocus cannot be formed, and myopia growth cannot be controlled. Therefore, the orthokeratology lens whose base curve has a spherical surface cannot form controllable, effective peripheral refractive power control. Therefore, it benefits only some of the patients and controls their myopia growth, but cannot achieve effective control of myopia of every patient.

Some of the existing orthokeratology lenses use an aspheric design. For example, Berke in U.S. Pat. No. 7,984,988 B2 designs the base curve zone of the orthokeratology lens as an ellipsoid; Sami G. E I Hage in U.S. Pat. No. 5,695,509 suggests determining key coordinate points according to the corneal shape and tear thickness, achieving aspheric fitting using the coordinate points, and determining the shape of the inner surface of the orthokeratology len. Patent 201420052256.2 designs the anterior surface of the orthokeratology lens as an aspheric surface to prevent the human eye from the interference of spherical aberration at night when wearing it so as to improve visual quality. The goals of these designs are all for the human eye to have better visual quality after shaping the cornea. The refractive power distribution of the entire eye is made to be as consistent at all apertures as possible, leading to hyperopic peripheral defocus. This is contrary to the purpose and method of controlling myopia through peripheral defocus.

Therefore, there is a particular need for an orthokeratology lens whose base curve zone is a special aspheric surface to achieve controllable myopic peripheral defocus to solve the aforesaid existing problem.

Intraocular lens mainly refers to a phakic intraocular lens (PIOL) for myopia refraction. PIOL is a negative-power lens implanted surgically between the cornea and lens of the human eye to correct refractive error of the human eye.

PIOLs are divided into anterior chamber type and posterior chamber type according to the implantation position. The posterior surface of the anterior chamber type is generally relatively flat and the anterior surface plays a major role in refraction. The anterior surface of the posterior chamber type is generally relatively flat, and the posterior surface plays a major role in refraction.

Existing PIOLs on the market use a spherical design. Patent 201520014249.8 discloses an aspheric PIOL, which aims to maintain the total refractive power of the human eye at different diameters at a constant value so as to achieve better visual quality. The refractive power provided by the negative diopter lens of a spherical design decreases (absolute value increases) as the aperture diameter increases, which causes the human eye to form hyperopic defocus and facilitates increase of the axial length of the human eye, thereby accelerating the development of myopia. Existing PIOLs of an aspheric design maintain the refractive power of the human eye at different diameters at a constant value, which compared with the curvature of the retina, would also form hyperopic defocus and thus accelerate the development of myopia.

Therefore, there is a particular need for an intraocular lens to solve the above-mentioned existing problem.

SUMMARY

An object of the present invention is to provide a method for preparing an aspheric vision correction lens with controllable peripheral defocus. In view of the shortcomings of the prior art, the distribution of the refractive power of the lens is determined by measuring the shape of the retina of the human eye or peripheral defocus of the human eye or the peripheral defocus with a lens, and a vision correction lens is made. When the vision correction lens is worn, and the refractive power of the vision correction lens is added to the human eye, the distribution of the refractive power of the entire eye on the retina is greater in the peripheral region of the retina than in the central region of the retina, and falls in front of the retina, to form myopic defocus and control myopic growth.

According to one aspect of the present invention, a method for preparing an aspheric vision correction lens with controllable peripheral defocus is provided. The method comprises the steps of:

(1) calculating and determining the conditions required for the formation of myopic defocus of a human eye, by examining the shape of the retina of the human eye, the amount of peripheral defocus of the naked human eye or the amount of peripheral defocus of the human eye with a lens;

(2) formulating a plan of distribution of the refractive power of the vision correction lens varying with the aperture, according to the conditions obtained for myopic defocus; and (3) making the vision correction lens according to the obtained plan of distribution of the refractive power of the vision correction lens such that after the refractive power of the vision correction lens is added to the human eye, the distribution of the refractive power of the entire eye on the retina is greater in the peripheral region of the retina than in the central region of the retina, and falls in front of the retina, to form myopic defocus.

In one embodiment of the present invention, in the above step (1), the shape of the retina of the human eye is measured by an ophthalmic test apparatus. If the ophthalmic test apparatus regards the retina as a spherical surface, the shape of the retina is measured by the radius of curvature of the retina. If the ophthalmic test apparatus regards the retina as an aspheric surface, the shape of the retina is measured by the equivalent radius of curvature of the aspheric surface. The equivalent radius of curvature of the aspheric surface is calculated in the following way:

$$r_m = \frac{\left(\frac{d_m}{2}\right)^2 + h_m^2}{2h_m} = \frac{(d_m)^2 + 4h_m^2}{8h_m},$$

wherein $d_m$ is the measured aperture, M is the point at the aperture $d_m$, $h_m$ is the sagittal height of point M, i.e., the difference in height between point M and the vertex of the aspheric surface, $r_m$ is the equivalent radius of curvature at point M.

In one embodiment of the present invention, in the above step (2), the distribution of the refractive power of the entire eye $D'_t$ formed by the vision correction lens and the human eye causes myopic defocus with respect to the shape of the retina, and meets:

$$\left|\frac{1}{D'_t}\right| < \left|\frac{1}{D_r}\right| = \left|\frac{1}{D_0} - r + \sqrt{R^2 - r^2}\right|$$

wherein $D_r$ is the refractive power of the entire eye at a radius r; $D_0$ is the refractive power of the entire eye at a small aperture (paraxial), i.e., the nominal value of the refractive power of the entire eye; r is the radius of the retina plane; R is the radius of curvature or equivalent radius of curvature of the retina.

In one embodiment of the present invention, the shape of the retina is measured by an optical coherence tomograph OCT or similar ophthalmic test apparatus.

In one embodiment of the present invention, in the above step (1), the amount of peripheral defocus of the naked human eye ($\Delta D1$) and the amount of peripheral defocus when a lens is worn ($\Delta D3$) are both measured by an ophthalmic test apparatus. The amount of peripheral defocus of the aspheric vision correction lens ($\Delta D2$) is known. When the amount of peripheral defocus provided by the vision correction lens ($\Delta D2$) plus the amount of peripheral defocus of the naked human eye ($\Delta D1$) is greater than or equal to 0, the human eye forms myopic peripheral defocus. When the amount of peripheral defocus of the human eye with a lens ($\Delta D3$) is greater than 0, it indicates that the amount of defocus of the trial lens meets the conditions for myopic peripheral defocus of the human eye.

In one embodiment of the present invention, when the amount of peripheral defocus of the human eye with a lens ($\Delta D3$) is less than or equal to 0, it indicates that the amount of defocus of the lens still puts the human eye in a state of hyperopic peripheral defocus, and the amount of defocus of the lens needs to be increased in order for the human eye to achieve myopic peripheral defocus.

In one embodiment of the present invention, the amount of peripheral defocus of the lens may be increased or decreased according to the patient's own physiological condition and requirement for the extent of myopia control, to achieve custom vision correction.

In one embodiment of the present invention, in the above step (3), according to the plan of refractive power distribution obtained in step (2), a vision correction lens is made using an aspheric design method. The expression of the aspheric surface is:

$$Z(y) = \frac{cy^2}{1 + \sqrt{1 - (1+Q)c^2 y^2}} + \sum_{i=2}^{5} A_{2i} \cdot y^{2i}$$

wherein Z(y) is an expression of the curve of the aspheric surface of the vision correction lens on the plane YZ; c is the reciprocal of the radius of curvature of the base spherical surface of the optical portion; y is the vertical distance from any point on the curve to the abscissa axis (Z); Q is aspheric coefficient; $A_{2i}$ is aspheric high-order term coefficient; and the points on the aspheric surface are obtained from the curve through rotationally symmetric variation about the abscissa axis (Z).

Through adjustment of the Q value and aspheric coefficients of the vision correction lens, the surface of the vision correction lens exhibits different equivalent curvatures in different radial portions, and the equivalent curvature changes uniformly and continuously throughout the optical zone, so that the vision correction lens has, at different apertures, a refractive power adapted to the refractive power distribution of myopic defocus, with the refractive power in the peripheral region being greater than the refractive power in the central region.

The equivalent radius of curvature is described by:

$$r_m = \frac{\left(\frac{d_m}{2}\right)^2 + h_m^2}{2h_m} = \frac{(d_m)^2 + 4h_m^2}{8h_m},$$

wherein $d_m$ is the measured aperture; M is the point at the aperture $d_m$; $h_m$ is the sagittal height of point M, i.e., the difference in height between point M and the vertex of the aspheric surface; and $r_m$ is the equivalent radius of curvature at point M.

Compared with the prior art, the method for preparing an aspheric vision correction lens with controllable peripheral defocus of the present invention controls the surface shape and curvature radius of the optical zone of the lens using an aspheric surface such that the vision correction lens changes uniformly in the direction of the aperture according to the set refractive power peripheral defocus amount, and the refractive power of the vision correction lens increases as the aperture increases, so as to provide the human eye with controllable myopic defocus and thus prevent increase in the axial length of the human eye and retard myopic growth, thereby accomplishing the object of the present invention.

Another object of the present invention is to provide a vision correction lens worn outside the eye. In view of the shortcomings of the prior art, an aspheric surface is used to control the surface shape and curvature radius of the optical zone of the lens such that the equivalent radius of curvature in the periphery is smaller than in the center, and the surface in the periphery is steeper than a spherical surface, and thereby the lens changes uniformly in the direction of the aperture according to the set refractive power distribution, and the refractive power of the lens increases as the aperture increases, providing the human eye with controllable myopic peripheral defocus and thereby preventing increase in the axial length of the human eye and retarding myopic growth.

According to a second aspect of the present invention, an aspheric vision correction lens prepared according to the above preparation method is provided. The vision correction lens is a correction lens worn outside the eye. At least one of a convex surface or a concave surface of the optical zone of the lens is aspheric. When the convex surface of the optical zone of the lens is aspheric, the absolute value of the equivalent radius of curvature of the periphery of the optical zone of the lens is smaller than the absolute value of the radius of curvature of the center of the optical zone of the lens. When the concave surface of the optical zone of the lens is aspheric, the absolute value of the equivalent radius of curvature of the periphery of the optical zone of the lens is greater than the absolute value of the radius of curvature of the center of the optical zone of the lens.

In one embodiment of the present invention, the shape of aspheric surface of the optical zone of the lens is defined by the scale factor η of equivalent radii of curvature, η being a ratio of r at different apertures $d_m$ and $d_n$, wherein m>n, $$\eta_{mn} = \frac{r_m}{r_n}$$

the equivalent radius of curvature of the optical zone of the lens is calculated in the following way:

$$r_m = \frac{\left(\frac{d_m}{2}\right)^2 + h_m^2}{2h_m} = \frac{(d_m)^2 + 4h_m^2}{8h_m},$$

wherein $d_m$ is the measured aperture; M is the point at the aperture $d_m$; $h_m$ is the sagittal height of point M, i.e., the difference in height between point M and the vertex of the aspheric surface; and $r_m$ is the equivalent radius of curvature at point M.

When the concave surface of the optical zone of the lens is an aspheric surface, the scale factor η of the equivalent radii of curvature of the aspheric surface is greater than 1. The scale factor $\eta_{53}$ of the equivalent radii of curvature of the aspheric surface at the 5 mm aperture and the 3 mm aperture is preferably greater than or equal to 1.002 and less than or equal to 1.086. When the convex surface of the optical zone of the lens is an aspheric surface, the scale factor η of the equivalent radii of curvature of the aspheric surface is less than 1. The scale factor $\eta_{53}$ of the equivalent radii of curvature of the aspheric surface at the 5 mm aperture and the 3 mm aperture is preferably greater than or equal to 0.682 and less than or equal to 0.986.

In one embodiment of the present invention, the refractive power of the lens in the air is less than or equal to 0D. The refractive power of the lens increases radially as the aperture increases, and the absolute value of the refractive power of the lens decreases as the aperture increases.

In one embodiment of the present invention, the difference between the refractive power of the lens at the 5 mm aperture and the refractive power of the lens at the 3 mm aperture $\Delta D_{53}$ is greater than or equal to 0.005D, preferably greater than or equal to 0.005D and less than or equal to 8.849D.

Compared with the prior art, for the vision correction lens worn outside the eye of the present invention, an aspheric surface is used to control the surface shape and curvature radius of the optical zone of the lens such that the vision correction lens changes uniformly in the direction of the aperture according to the set refractive power distribution, the refractive power of the vision correction lens increases as the aperture increases, and the absolute value of the refractive power decreases as the aperture increases, so as to provide the human eye with controllable myopic peripheral defocus and thus prevent increase in the axial length of the human eye and retard myopic growth, thereby accomplishing the object of the present invention.

Another object of the present invention is to provide an orthokeratology lens. In view of the shortcomings of the prior art, an aspheric surface is used to control the surface shape and curvature radius of the optical zone of the lens such that the absolute value of the equivalent radius of curvature in the periphery is smaller than in the center, and the surface in the periphery is steeper than a spherical surface, and thereby the lens changes uniformly in the direction of the aperture according to the set refractive power distribution, and the refractive power of the lens increases as the aperture increases, providing the human eye with controllable myopic defocus and thereby preventing increase in the axial length of the human eye and retarding myopic growth.

According to a third aspect of the present invention, an aspheric vision correction lens prepared according to the above preparation method is provided. The vision correction lens is an orthokeratology lens, characterized in that, the aspheric surface of the base curve zone of the lens is defined by the scale factor η of equivalent radii of curvature. The scale factor η of the equivalent radii of curvature of the aspheric surface is less than 1. The scale factor $\eta_{53}$ of the equivalent radii of curvature of the aspheric surface of the base curve zone of the lens at the 5 mm aperture and the 3 mm aperture is preferably greater than or equal to 0.67 and less than 1, and more preferably greater than or equal to 0.67 and less than or equal to 0.998.

The scale factor η is a ratio of r of the lens at different diameters $d_m$ and $d_n$, wherein m>n, $$\eta_{mn} = \frac{r_m}{r_n}$$

the equivalent radius of curvature of the base curve zone of the lens is calculated in the following way:

$$r_m = \frac{\left(\frac{d_m}{2}\right)^2 + h_m^2}{2h_m} = \frac{(d_m)^2 + 4h_m^2}{8h_m},$$

wherein $d_m$ is the measured aperture; M is the point at the aperture $d_m$; $h_m$ is the sagittal height of point M, i.e., the difference in height between point M and the vertex of the aspheric surface; and $r_m$ is the equivalent radius of curvature at point M.

Compared with the prior art, for the orthokeratology lens of the present invention, an aspheric surface is used to control the surface shape and curvature radius of the base curve zone of the lens such that the absolute value of the equivalent radius of curvature in the periphery is smaller than in the center, and the surface in the periphery is steeper than a spherical surface. After overnight wearing, the anterior surface of the cornea of the human eye is shaped into the shape of the base curve zone of the orthokeratology lens, so as to provide the human eye with controllable myopic defocus, and thus prevent increase in the axial length of the human eye and retard myopic growth, thereby accomplishing the object of the present invention.

Another object of the present invention is to provide an intraocular lens. In view of the shortcomings of the prior art, an aspheric surface is used to control the surface shape and curvature radius of the optical zone of the lens such that the curvature radius changes uniformly at different apertures, and the absolute value of the equivalent radius of curvature in the periphery is greater than in the center, whereby the refractive power in the periphery is greater than in the center (the absolute value of the refractive power in the periphery is smaller than in the center), and the refractive power distribution exhibits uniform change and causes myopic peripheral defocus, thereby controlling the myopia growth of the myopic patient.

According to a fourth aspect of the present invention, an aspheric vision correction lens prepared according to the above preparation method is provided. The vision correction lens is an intraocular lens, characterized in that, at least one of an anterior surface or a posterior surface of the optical zone of the lens is an aspheric surface. The lens changes uniformly in the direction of the aperture according to the set refractive power peripheral defocus amount. The refractive power of the lens increases as the aperture increases, and the absolute value of the refractive power decreases as the aperture increases. The refractive power of the lens in the aqueous humor is less than or equal to 0D.

In one embodiment of the present invention, the shape of the aspheric surface of the optical zone of the lens is defined by the scale factor η of equivalent radii of curvature. The scale factor η of the equivalent radii of curvature of the aspheric surface is greater than 1. The scale factor $\eta_{43}$ of the equivalent radii of curvature of the aspheric surface of the optical zone of the lens at the 4 mm aperture and the 3 mm aperture is preferably greater than or equal to 1.005, and more preferably greater than or equal to 1.002 and less than or equal to 1.09.

Scale factor η is a ratio of r of the lens at different diameters $d_m$ and $d_n$, wherein m>n, $$\eta_{mn} = \frac{r_m}{r_n}$$

the equivalent radius of curvature of the optical zone of the lens is calculated in the following way:

$$r_m = \frac{\left(\frac{d_m}{2}\right)^2 + h_m^2}{2h_m} = \frac{(d_m)^2 + 4h_m^2}{8h_m},$$

wherein $d_m$ is the measured aperture; M is the point at the aperture $d_m$; $h_m$ is the sagittal height of point M, i.e., the difference in height between point M and the vertex of the aspheric surface; and $r_m$ is the equivalent radius of curvature at point M.

Compared with the prior art, for the intraocular lens of the present invention, by means of surface shape structure of an aspheric surface, an aspheric surface is used to control the surface shape and curvature radius of the optical zone of the lens such that the curvature radius exhibits a uniform change at different apertures, and the absolute value of the equivalent radius of curvature in the periphery is greater than in the center, whereby the refractive power in the periphery is greater than in the center, the absolute value of the refractive power in the periphery is smaller than in the center, and the refractive power distribution exhibits uniform change and causes myopic peripheral defocus, thereby controlling the myopia growth of the myopic patient and accomplishing the object of the present invention.

According to a fifth aspect of the present invention, a diagnosis and treatment method that utilizes myopic peripheral defocus to control and retard myopia growth is provided. It is characterized in that the diagnosis and treatment method is realized by using an aspheric vision correction lens prepared according to the above preparation method.

The features of the present invention can be clearly understood with reference to the drawings in the present application and the following detailed description of the preferred embodiments.

DETAILED DESCRIPTION OF EMBODIMENTS

Figure 1:
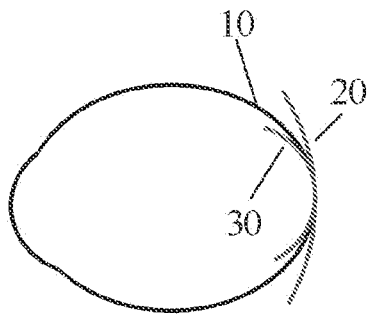
FIG. 1 is a schematic diagram of the retina, myopic defocus and hyperopic defocus.

For easy understanding of the technical means, creative features, objects and effects of the present invention, the present invention will be further described below with reference to the specific drawings.

Definitions of the Terms

The term "myopic peripheral defocus" as used in the present application means that the peripheral region has a refractive power greater than that of the central region. When the central image points fall on the retina, the peripheral image points fall in front of the retina, it is defined that the amount of peripheral defocus ΔD is greater than 0.

The term "hyperopic peripheral defocus" as used in the present application means that the peripheral region has a refractive power less than that of the central region. When the central image points fall on the retina, the peripheral image points fall behind of the retina, it is defined that the amount of defocus ΔD is less than 0.

The term "refractive power", as used in this application, is a measurement of the degree to which a lens refracts light. "Diopter" is a measurement of the magnitude of the refractive power. There are positive and negative diopters. The signs are also taken into account when comparing the diopters. For example, where D1=10.0D and D2=15.0D, D1<D2; where D3=−10.0D and D4=−15.0D, D3>D4.

The term "optical zone" as used in the present application refers to the main functional portion in the central region of the lens that has optical properties and can thus achieve adjustment of the diopter of the lens.

The term "haptic" or "support haptic" as used in the present application refers to the portion that is connected with the optical portion of the lens and functions to support the optical portion and position the lens in the human eye.

The term "radial" as used in the present application refers to the direction of a straight line from the lens center along the radius or diameter.

The term "aperture" as used in the present application refers to the radial diameter of the lens surface.

Terms indicating positional relationship in the present application, such as "anterior" and "posterior" are used based on the distance to the surface of the cornea of the eye. For example, for a lens of the present application, the "posterior surface of the optical portion" is an optical surface that is closer to the cornea of the eye than the "anterior surface of the optical portion".

The term "base spherical surface" as used in the present application refers to an ideal spherical surface having the same designed value of radius of curvature corresponding to the various shapes taken by the anterior and posterior surfaces of the optical portion of the lens. In the present application, in order to make the terms consistent, the ideal spherical surfaces are collectively referred to as "base spherical surface".

The terms "steep" and "flat" as used in the present application are descriptions of the greatness of the equivalent radius of curvature of the lens. For example, in the present application, "steeper than the spherical surface" means that the absolute value of the equivalent radius of curvature of the lens is smaller than the absolute value of the radius of curvature of the base spherical surface; and "flatter than the spherical surface" means that the absolute value of the equivalent radius of curvature of the lens is greater than the absolute value of the radius of curvature of the base spherical surface.

The term "convex surface" as used in the present application refers to a surface which is always below the tangent plane made through any point on the surface; "concave surface" refers to a surface which is always above the tangent plane made through any point on the surface.

Figure 6:
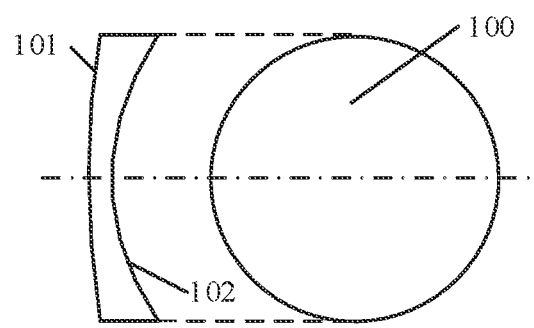
FIG. 6 is a schematic diagram of the structure of Example 2 of the present invention.

Similar to shown in FIG. 6, a vision correction glasses worn outside the eye according to one aspect of the present invention comprise a lens. At least one of the convex surface 101 or the concave surface 102 of the optical zone 100 of the lens is aspheric. When the convex surface 101 of the optical zone 100 of the lens is aspheric, the equivalent radius of curvature of the periphery of the optical zone 100 of the lens is smaller than the radius of curvature of the center of the optical zone 100 of the lens; and when the concave surface 102 of the optical zone 100 of the lens is aspheric, the equivalent radius of curvature of the periphery of the optical zone 100 of the lens is greater than the radius of curvature of the center of the optical zone 100 of the lens.

Figure 2:
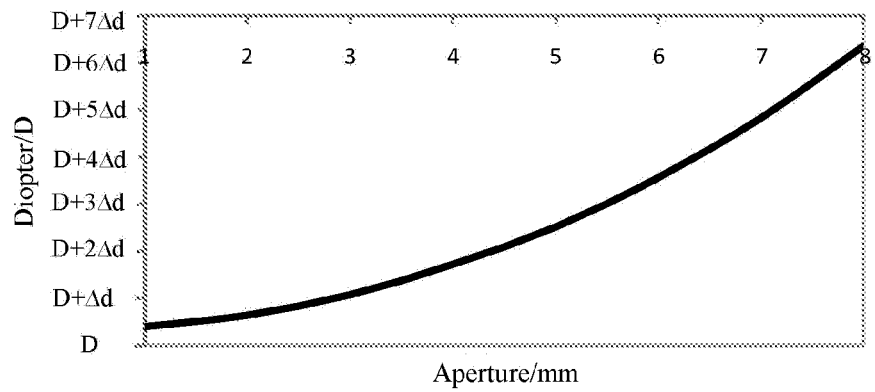
FIG. 2 is a schematic diagram of a curve of distribution of diopter of myopic peripheral defocus of the present invention.

As shown in FIG. 2, the refractive power of the lens in the air is less than or equal to 0D. The refractive power of the lens increases radially as the aperture increases, and the absolute value of the refractive power of the lens decreases as the aperture increases.

Figure 7:
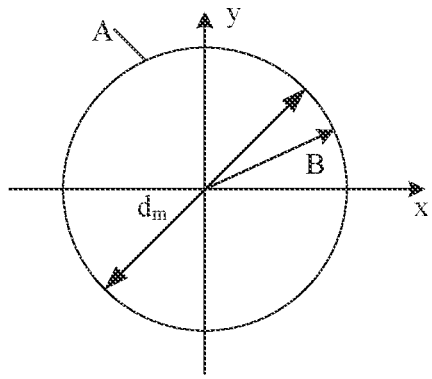
FIG. 7 is a radial schematic diagram of the lens of the present invention.

FIG. 7 is a radial schematic diagram of a lens of the present invention, wherein A is a front view of the lens of the present invention, and B shows the radial direction of the lens of the present invention.

The difference between the refractive power of the lens at the 5 mm aperture and the refractive power of the lens at the 3 mm aperture $\Delta D_{53}$ is greater than or equal to 0.005D, preferably greater than or equal to 0.005D and less than or equal to 8.849D.

Figure 3:
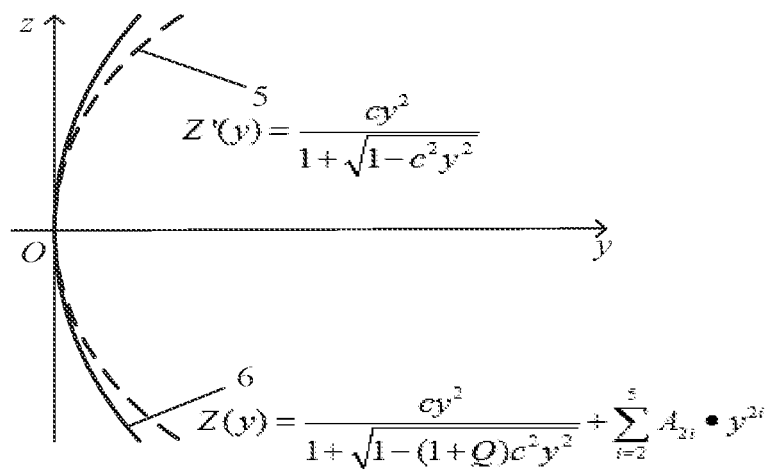
FIG. 3 is a schematic diagram of an expression of the curve of an aspheric surface of the present invention.

As shown in FIG. 3, the expression of the aspheric surface of the optical zone 100 of the lens is:

$$Z(y) = \frac{cy^2}{1+\sqrt{1-(1+Q)c^2y^2}} + \sum_{i=2}^{5} A_{2i} \cdot y^{2i}$$

wherein c is the reciprocal of the radius of curvature of the base spherical surface of the optical portion, y is the vertical distance from any point on the curve to the abscissa axis (Z), Q is aspheric coefficient, $A_{2i}$ is aspheric high-order term coefficient, and the aspheric surface is obtained from the aspheric surface curve through rotationally symmetric variation about the abscissa axis (Z).

Figure 4:
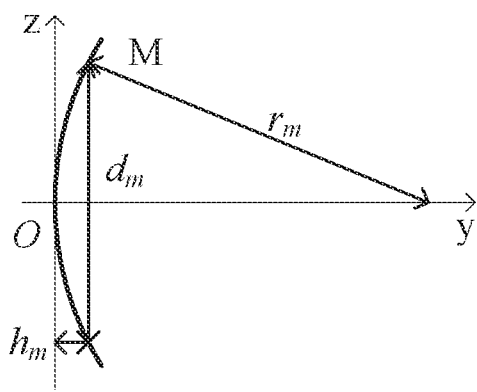
FIG. 4 is a schematic diagram of the parameters to which the scale factor η of the present invention is related.

As shown in FIG. 4, the shape of the aspheric surface of the optical zone 100 of the lens is defined by the scale factor η of equivalent radii of curvature, and η is a ratio of r at different apertures $d_m$ and $d_n$, wherein m>n, $$\eta_{mn} = \frac{r_m}{r_n}$$

When the concave surface 102 of the optical zone 100 of the lens is an aspheric surface, the scale factor η of the equivalent radii of curvature of the aspheric surface is greater than 1. When the convex surface 101 of the optical zone 100 of the lens is an aspheric surface, the scale factor η of the equivalent radii of curvature of the aspheric surface is less than 1.

The equivalent radius of curvature of the optical zone 100 of the lens is calculated in the following way:

$$r_m = \frac{\left(\frac{d_m}{2}\right)^2 + h_m^2}{2h_m} = \frac{(d_m)^2 + 4h_m^2}{8h_m},$$

wherein $d_m$ is the measured aperture, M is the point at the aperture $d_m$, $h_m$ is the sagittal height of point M, i.e., the difference in height between point M and the vertex of the aspheric surface, and $r_m$ is the equivalent radius of curvature at point M.

When the concave surface 102 of the optical zone 100 of the lens is an aspheric surface, the scale factor $\eta_{53}$ of the equivalent radii of curvature of the aspheric surface at the 5 mm aperture and the 3 mm aperture is preferably greater than or equal to 1.002 and less than or equal to 1.086.

When the convex surface 101 of the optical zone 100 of the lens is an aspheric surface, the scale factor $\eta_{53}$ of the equivalent radii of curvature of the aspheric surface at the 5 mm aperture and the 3 mm aperture is preferably greater than or equal to 0.682 and less than or equal to 0.986.

For specific examples, see Table 1, wherein Rp and Qp are the radius of curvature and aspheric coefficient of the convex surface (the surface in direct contact with the cornea) of the contact lens; Ra, Qa, A4, A6 and A8 are the radius of curvature, aspheric coefficient and higher-order aspheric coefficients of the anterior surface of the contact lens, respectively; $\Delta D_{53}$ is the difference between the refractive power of the lens at the 5 mm aperture and the refractive power of the lens at the 3 mm aperture; and $\eta_{53}$ is a scale factor of the equivalent radii of curvature of the aspheric surface of the lens at the 5 mm aperture and the 3 mm aperture.

TABLE 1

Examples of Cornea Contact Lenses

| Refractive index | Diopter/D | Rp/mm | Qp | Ra/mm | Qa | A4 | A6 | A8 | $\Delta D_{53}$ | $\eta_{53}$ |
|---|---|---|---|---|---|---|---|---|---|---|
| 1.415 | −20 | 10.00 | −0.25 | 19.581 | 2.412 | 5.402E−05 | −3.762E−08 | −1.091E−09 | 0.130 | 0.986 |
| 1.400 | −30 | 11.166 | 0 | 76.890 | 291.247 | 2.553E−04 | 1.612E−06 | −1.875E−07 | 1.690 | 0.835 |
| 1.400 | −30 | 11.166 | 0 | 93.392 | 772.250 | 7.205E−04 | 4.236E−06 | −1.721E−06 | 4.723 | 0.682 |
| 1.500 | −30 | 10 | 0 | 27.443 | 31.184 | 5.526E−04 | −5.714E−06 | −2.844E−07 | 4.757 | 0.875 |
| 1.400 | −30 | 10 | 0 | 48.019 | 185.239 | 6.685E−04 | 1.051E−06 | −1.972E−06 | 4.734 | 0.779 |
| 1.400 | −30 | 10 | 0 | 43.144 | 86.798 | 2.367E−04 | 8.245E−07 | −2.729E−07 | 1.715 | 0.887 |
| 1.400 | −10 | 10 | 0 | 13.539 | 1.401 | 9.163E−05 | 6.267E−07 | −8.348E−11 | 0.714 | 0.982 |
| 1.400 | −30 | 10 | 0 | 42.604 | 67.215 | 1.931E−04 | 2.685E−07 | −9.757E−08 | 1.188 | 0.907 |
| 1.400 | −10 | 10 | 0 | 13.512 | 1.277 | 6.053E−05 | 3.763E−07 | 3.089E−09 | 0.452 | 0.986 |
| 1.400 | −30 | 10 | 0 | 41.966 | 52.149 | 1.393E−04 | −1.554E−07 | −4.106E−07 | 0.618 | 0.929 |
| 1.432 | −15 | 5 | 0 | 6.194 | 0.199 | 3.103E−04 | 3.952E−06 | 3.853E−07 | 0.269 | 0.980 |
| 1.432 | −15 | 7.8 | 0 | 10.859 | 0.664 | 1.035E−04 | 5.140E−07 | 1.131E−08 | 0.191 | 0.986 |
| 1.432 | −30 | 5 | 0 | 7.970 | 1.175 | 4.929E−04 | 4.910E−06 | 1.295E−07 | 0.868 | 0.952 |
| 1.432 | −30 | 7.8 | 0 | 17.585 | 2.136 | 2.707E−04 | 1.162E−06 | 1.410E−08 | 0.570 | 0.957 |
| 1.432 | −30 | 10 | 0 | 33.922 | 25.348 | 1.168E−04 | −4.114E−09 | −2.754E−08 | 0.476 | 0.949 |
| 1.432 | −15 | 5 | 0 | 6.192 | 0.230 | 3.032E−04 | 3.710E−06 | 3.520E−07 | 0.352 | 0.966 |
| 1.432 | −15 | 10 | 0 | 15.536 | 1.451 | 6.693E−05 | 2.190E−07 | 5.918E−09 | 0.253 | 0.976 |
| 1.432 | −30 | 5 | 0 | 7.982 | 1.132 | 5.279E−04 | 4.478E−06 | 2.113E−07 | 1.005 | 0.920 |
| 1.432 | −30 | 10 | 0 | 34.020 | 28.649 | 1.254E−04 | −1.425E−07 | −2.733E−08 | 0.623 | 0.909 |
| 1.432 | −30 | 5 | 0 | 8.006 | 1.496 | 5.064E−04 | 3.737E−06 | −9.895E−08 | 1.539 | 0.947 |
| 1.432 | −30 | 10 | 0 | 34.391 | 35.500 | 1.763E−04 | 2.033E−07 | −5.459E−08 | 1.190 | 0.927 |
| 1.432 | −30 | 5 | 0 | 8.026 | 1.498 | 5.799E−04 | 3.795E−06 | −1.053E−07 | 2.032 | 0.944 |
| 1.432 | −30 | 10 | 0 | 34.753 | 42.723 | 2.232E−04 | 9.326E−07 | −1.499E−07 | 1.723 | 0.911 |
| 1.432 | −30 | 5 | 0 | 8.047 | 1.581 | 6.355E−04 | 2.547E−06 | −1.434E−07 | 2.490 | 0.941 |
| 1.432 | −30 | 10 | 0 | 30.107 | 46.095 | 2.828E−04 | 1.180E−06 | −1.965E−07 | 2.209 | 0.890 |
| 1.432 | −30 | 5 | 0 | 8.075 | 1.922 | 6.570E−04 | 2.717E−06 | −4.791E−07 | 3.128 | 0.936 |
| 1.432 | −30 | 10 | 0 | 35.665 | 69.042 | 3.237E−04 | −4.695E−07 | −5.382E−07 | 2.879 | 0.877 |
| 1.432 | −30 | 10 | 0 | 37.482 | 118.917 | 5.157E−04 | 1.713E−06 | −2.677E−06 | 4.779 | 0.823 |
| 1.432 | −30 | 5 | −0.25 | 7.985 | 0.952 | 3.945E−04 | 4.615E−07 | −7.752E−08 | 1.502 | 0.963 |
| 1.432 | −30 | 10 | −0.25 | 34.219 | 32.089 | 1.536E−04 | 1.739E−07 | −3.938E−08 | 0.582 | 0.935 |
| 1.432 | −30 | 5 | −0.25 | 8.017 | 1.008 | 4.586E−04 | −8.108E−08 | −9.179E−08 | 2.001 | 0.960 |
| 1.432 | −30 | 10 | −0.25 | 34.763 | 40.819 | 2.014E−04 | 1.339E−07 | −9.593E−08 | 1.470 | 0.918 |
| 1.432 | −30 | 5 | −0.5 | 8.016 | 0.718 | 2.862E−04 | −2.794E−06 | −1.090E−07 | 1.981 | 0.974 |
| 1.432 | −30 | 10 | −0.5 | 34.765 | −37.245 | 1.816E−04 | 1.326E−07 | −6.647E−08 | 1.712 | 0.925 |
| 1.432 | −30 | 10 | −1 | 34.770 | 31.281 | 1.385E−04 | 2.832E−07 | −2.820E−08 | 1.707 | 0.939 |
| 1.710 | −30 | 10 | 0 | 18.205 | 9.161 | 3.391E−04 | −4.381E−06 | −1.337E−07 | 4.739 | 0.934 |

Example 1

Figure 5:
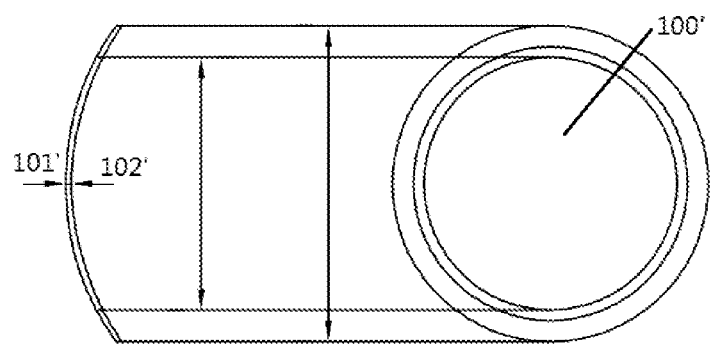
FIG. 5 is a schematic diagram of the structure of Example 1 of the present invention.

As shown in FIG. 5, in this example, the vision correction lens is a cornea contact lens. The shape of the concave surface 102' (the surface in direct contact with the cornea) of the optical zone 100' of the lens is consistent with the shape the surface of the cornea, namely a spherical surface or aspheric surface consistent with the form of the cornea. The convex surface 101' of the optical zone 100' of the lens has an aspheric structure of the present invention. The aspheric structure of the present invention is as described above.

In this example, the scale factor $\eta_{53}$ of the equivalent radii of curvature of the aspheric surface at the 5 mm aperture and the 3 mm aperture is preferably greater than or equal to 0.682 and less than or equal to 0.986, and the difference in the refractive power $\Delta D53$ is greater than or equal to 0.130D and less than or equal to 4.779D.

Example 2

In this example, the vision correction lens is frame glasses. At least one of the convex surface 101 or the concave surface 102 of the optical zone 100 of the lens has the aspheric surface structure of the present invention as described above.

The convex surface 101 of the optical zone 100 of the lens has the aspheric surface structure of the present invention. The structure is similar to that in Example 1. The equivalent radius of curvature in the periphery is smaller than in the center, and the surface in the periphery is steeper than a spherical surface such that the surface changes uniformly in the direction of the aperture according to the set refractive power distribution.

As shown in FIG. 6, when the aspheric surface structure of the present invention is on the concave surface 102 of the optical zone 100 of the lens, since the surface on which the aspheric surface is located provides the lens with a negative refractive power, the absolute value of the refractive power provided by the lens at a larger aperture should be smaller than that at a smaller aperture in order for the lens to have a refractive power distribution the same as that of the present invention. In order to achieve the same refractive power control, the surface in the periphery should obviously be flatter than the spherical surface.

In this example, the scale factor $\eta_{53}$ of the equivalent radii of curvature of the aspheric surface at the 5 mm aperture and the 3 mm aperture is preferably greater than or equal to 1.002 and less than or equal to 1.086, and the difference in the refractive power $\Delta D53$ is greater than or equal to 0.005D and less than or equal to 8.849D.

For specific examples, see Table 2, wherein Rp and Qp are the radius of curvature and aspheric coefficient of the convex surface (the surface in direct contact with the cornea) of the contact lens; Ra, Qa, A4, A6 and A8 are the radius of curvature, aspheric coefficient and higher-order aspheric coefficients of the convex surface of the contact lens, respectively; $\Delta D_{53}$ is the difference between the refractive power of the lens at the 5 mm aperture and the refractive power of the lens at the 3 mm aperture; and $\eta_{53}$ is a scale factor of the equivalent radii of curvature of the aspheric surface of the lens at the 5 mm aperture and the 3 mm aperture.

TABLE 2

Examples of Frame Glasses

| Refractive index | Ra | Rp | Qp | A4 | A6 | A8 | $\Delta D_{53}$ | $\eta_{53}$ |
|---|---|---|---|---|---|---|---|---|
| 1.43 | 10.428 | 6.869 | −0.727 | −3.81E−04 | −1.33E−06 | 2.85E−08 | 3.047 | 1.036 |
| 1.43 | 10.428 | 6.869 | −1.000 | 0 | 0 | 0 | 1.040 | 1.021 |
| 1.43 | 10.428 | 6.869 | −2.000 | 0 | 0 | 0 | 3.429 | 1.040 |
| 1.43 | 10.428 | 6.869 | −5.000 | 0 | 0 | 0 | 7.939 | 1.086 |
| 1.50 | 9.773 | 7.000 | −5.000 | 0 | 0 | 0 | 8.662 | 1.083 |
| 1.70 | 8.807 | 7.000 | −5.000 | 0 | 0 | 0 | 8.849 | 1.083 |
| 1.43 | 8.368 | 5.502 | 0.215 | −7.247E−04 | −1.067E−05 | −1.003E−06 | 0.392 | 1.024 |
| 1.55 | 7.724 | 5.954 | −0.157 | −2.029E−04 | −2.378E−06 | −9.978E−08 | 0.227 | 1.014 |
| 1.71 | 7.275 | 5.964 | −0.123 | −1.562E−04 | −1.820E−06 | −9.407E−08 | 0.225 | 1.011 |
| 1.71 | 6.203 | 5.996 | −0.019 | −2.161E−05 | −1.861E−07 | −2.286E−08 | 0.005 | 1.002 |

Of course, for the frame glasses, both the convex surface and the concave surface of the lens may be of the aspheric surface structure of the present invention, besides that only one of them has the aspheric surface structure of the present invention. It is unnecessary to repeat the details here.

On the basis of the present invention's concept of controlling myopic growth by myopic peripheral defocus and aspheric surface design of the lens, those skilled in the art may also conceive making, through contrary modified control of the lens, the absolute value of the refractive power of the lens at a larger aperture greater than that at a smaller aperture, to achieve hyperopic peripheral defocus of the human eye to thereby treat hyperopia by actively facilitating increase of the axial length of the human eye.

Figure 8:
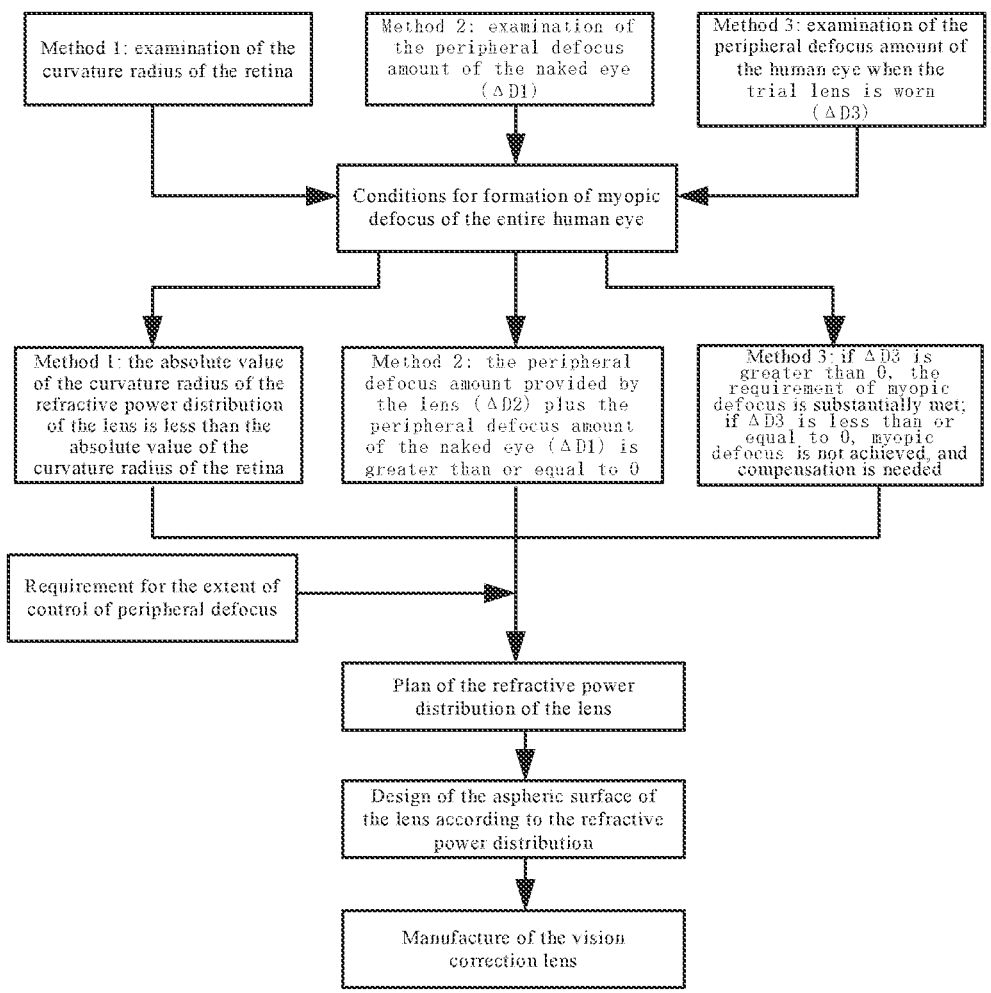
FIG. 8 is a flow diagram of a vision correction lens diagnosis and treatment method of the present invention.

As shown in FIG. 8, a method for preparing an aspheric vision correction lens with controllable peripheral defocus according to one aspect of the present invention comprises the steps of:
(1) calculating and determining the conditions required for the formation of myopic defocus of a human eye by examining the shape of the retina of the human eye, the amount of peripheral defocus of the naked human eye or the amount of peripheral defocus of the human eye with a lens;
(2) formulating a plan of distribution of the refractive power of the vision correction lens varying with the aperture, according to the conditions obtained for myopic defocus; and
(3) manufacturing a vision correction lens according to the obtained plan of distribution of the refractive power of the vision correction lens such that after the refractive power of the vision correction lens is added to the human eye, the distribution of the refractive power of the entire eye on the retina is greater in the peripheral region of the retina than in the central region, and falls in front of the retina, to form myopic defocus.

Figure 9:
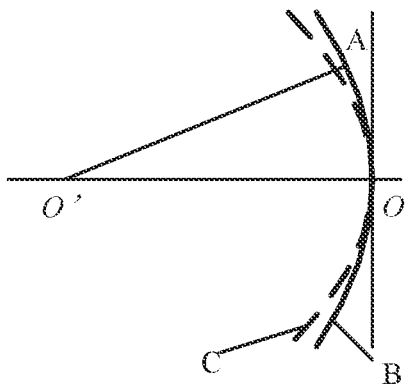
FIG. 9 is a schematic diagram of the retina and refractive power distribution of the present invention.

As shown in FIG. 9, B is the retina, and C is the curve of distribution of the refractive power of the entire eye on the retina. The shape of the retina, the amount of peripheral defocus of the naked human eye and the amount of peripheral defocus of the human eye with a lens may be measured by an ophthalmic test apparatus.

The shape of the retina of the human eye is measured by an ophthalmic test apparatus (such as an Optical Coherence Tomograph OCT). The ophthalmic test apparatus regards the retina as a spherical surface, and measures the shape of the retina by its radius of curvature.

The shape of the retina of the human eye is measured by an ophthalmic test apparatus. The ophthalmic test apparatus regards the retina as an aspheric surface, and measures the shape of the retina by the equivalent radius of curvature of the aspheric surface. The equivalent radius of curvature of the aspheric surface is calculated in the following way $$r_m = \frac{\left(\frac{d_m}{2}\right)^2 + h_m^2}{2h_m} = \frac{(d_m)^2 + 4h_m^2}{8h_m},$$

wherein $d_m$ is the measured aperture; M is the point at the aperture $d_m$; $h_m$ is the sagittal height of point M, i.e., the difference in height between point M and the vertex of the aspheric surface; and $r_m$ is the equivalent radius of curvature at point M.

The distribution of the refractive power of the entire eye formed by the vision correction lens and the human eye meets:

$$\frac{1}{D_r} = \frac{1}{D_0} - r + \sqrt{R^2 - r^2}$$

The distribution of the refractive power of the entire eye formed by the vision correction lens and the human eye causes myopic defocus with respect to the shape of the retina, and meets:

$$\left|\frac{1}{D'_t}\right| < \left|\frac{1}{D_r}\right| = \left|\frac{1}{D_0} - r + \sqrt{R^2 - r^2}\right|$$

wherein $D_r$ is the refractive power of the entire eye at a radius r; $D_0$ is the refractive power of the entire eye at a small aperture (paraxial), i.e., the nominal value of the refractive power of the entire eye; r is the radius of the retina plane; R is the radius of curvature or equivalent radius of curvature of the retina.

Under the above conditions, the distribution of the refractive power of the entire eye on the retina is shown as curve C in FIG. 9. Through the aspheric design, the difference between the refractive power at the edge of the lens and the refractive power at the center of the lens meets the above requirements.

According to the obtained conditions that the refractive power distribution meets, a vision correction lens is made using the aspheric design method such that the refractive power of the vision correction lens has a myopic defocus distribution at different apertures, i.e., the refractive power increases as the aperture increases (as shown in FIG. 2).

The amount of peripheral defocus of a naked human eye (ΔD1) may be measured by an ophthalmic test apparatus (such as OCT, corneal topographer, wavefront aberrometer and the like). When the amount of peripheral defocus provided by the vision correction lens (ΔD2) plus the amount of peripheral defocus of the naked human eye (ΔD1) is greater than or equal to 0, the human eye forms myopic peripheral defocus.

A trial lens of a known diopter and a known refractive power distribution may be worn on the human eye. The amount of peripheral defocus of the human eye with a lens (ΔD3) is examined when the lens is worn. The amount of peripheral defocus of the human eye with a lens (ΔD3) may be measured by an ophthalmic test apparatus. When the amount of peripheral defocus of the human eye with a lens (ΔD3) is greater than 0, it indicates that the amount of defocus of the trial lens already meets the conditions for the human eye to have myopic peripheral defocus, and a vision correction lens may be made accordingly. When the amount of peripheral defocus of the human eye with a lens (ΔD3) is less than or equal to 0, it indicates that the amount of defocus of the lens still puts the human eye in a state of hyperopic peripheral defocus, and the amount of defocus of the lens needs to be increased in order for the human eye to achieve myopic peripheral defocus.

The amount of peripheral defocus of the lens may be increased or decreased according to the patient's own physiological condition and requirements for the extent of myopia control, to achieve custom vision correction.

According to the refractive power distribution plan obtained in step (2), a vision correction lens is made using the aspheric design method such that the refractive power of the vision correction lens has a myopic defocus distribution at different apertures, i.e., the refractive power increases as the aperture increases. The expression of the aspheric surface (as shown in FIG. 3, D is the spherical surface curve, and E is the aspheric surface curve) is:

$$Z(y) = \frac{cy^2}{1 + \sqrt{1 - (1+Q)c^2 y^2}} + \sum_{i=2}^{5} A_{2i} \cdot y^{2i}$$

wherein Z(y) is an expression of the curve of the aspheric surface of the vision correction lens on the plane YZ, c is the reciprocal of the radius of curvature of the base spherical surface of the optical portion, y is the vertical distance from any point on the curve to the abscissa axis (Z), Q is aspheric coefficient, $A_{2i}$ is aspheric high-order term coefficient, and the points on the aspheric surface are obtained from the curve through rotationally symmetric variation about the abscissa axis (Z).

Through adjustment of the Q value and aspheric coefficients of the vision correction lens, the surface of the vision correction lens exhibits different equivalent curvatures in different radial portions, and the equivalent curvature changes uniformly and continuously throughout the optical zone, so that the vision correction lens has, at different apertures, a refractive power adapted to the refractive power distribution of myopic defocus, with the refractive power in the peripheral region being greater than the refractive power in the central region.

It further comprises a method for controlling the shape of an aspheric surface. The method is described by the scale factor η of equivalent curvature radii (as shown in FIG. 4).

$$\eta_{mn} = \frac{r_m}{r_n}$$

η is the ratio of r at different apertures $d_m$ and $d_n$, wherein m>n.

For a spherical surface, η=1; for an aspheric surface which is flatter in the periphery than in the center, η>1; for an aspheric surface which is steeper in the periphery than in the center, η<1. The equivalent radius of curvature of the aspheric surface at each aperture is designed through control of the scale factor of the equivalent radii of curvature, thereby enabling the refractive power distribution of the lens to meet the requirements of myopic peripheral defocus.

It is expressed using the difference in refractive power of the lens at different apertures in the air.

$$\Delta D_{m,n} = D_m - D_n$$

It represents the difference between the refractive power of the lens at an aperture of m and at an aperture of n, wherein m>n.

The present invention also provides an aspheric vision correction lens, which includes a vision correction lens worn outside the eye, an orthokeratology lens and an intraocular lens. The aspheric vision correction lens is made using the method for preparing an aspheric vision correction lens of the present invention.

The present invention also provides a diagnosis and treatment method that utilizes myopic peripheral defocus to control and retard myopia growth. The diagnosis and treatment method is realized by using an aspheric vision correction lens prepared in the method for preparing an aspheric vision correction lens of the present invention.

Example 3

In this example, the vision correction lens is a vision correction lens worn outside the eye (such as frame glasses).

Figure 10:
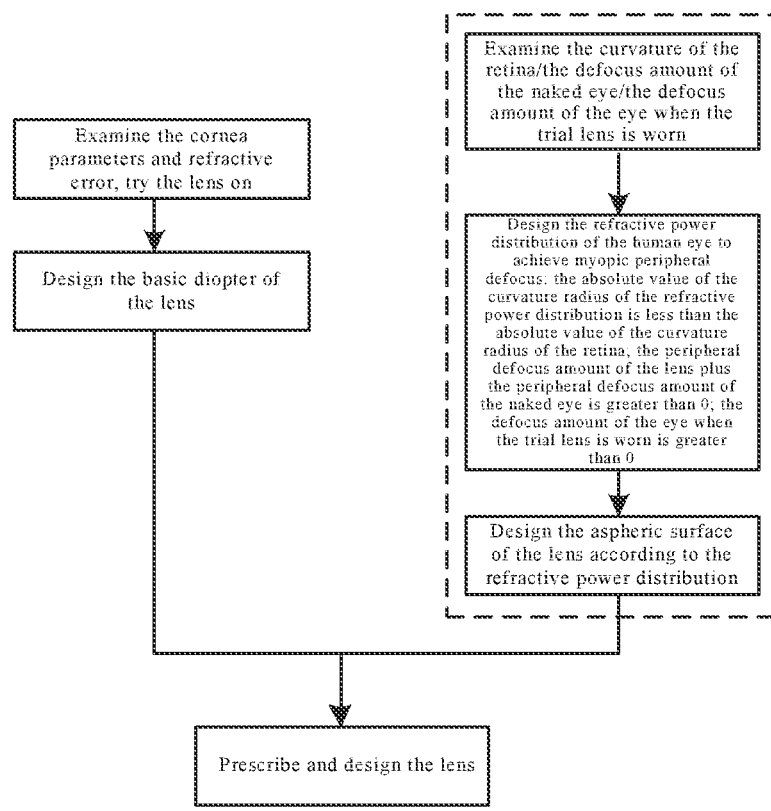
FIG. 10 is a flow diagram of Example 3 of the present invention.

As shown in FIG. 10, in this example, in addition to the existing fitting methods of frame glasses, RGP, it further comprises a method for preparing an aspheric vision correction lens with controllable peripheral defocus of the present invention, which comprises the following steps:
(1) calculating and determining the conditions required for the formation of myopic defocus of a human eye by examining the shape of the retina of the human eye, the amount of peripheral defocus of the naked human eye or the amount of peripheral defocus of the human eye with a lens;
(2) formulating a plan of distribution of the refractive power of the vision correction lens varying with the aperture, according to the conditions obtained for myopic defocus; and
(3) manufacturing a vision correction lens according to the obtained plan of distribution of the refractive power of the vision correction lens such that after the refractive power of the vision correction lens is added to the human eye, the distribution of the refractive power of the entire eye on the retina is greater in the peripheral region of the retina than in the central region, and falls in front of the retina, to form myopic defocus.

The rest of the contents are the same as above, so it is not repeated here.

Example 4

In this example, the vision correction lens is an orthokeratology lens.

Figure 11:
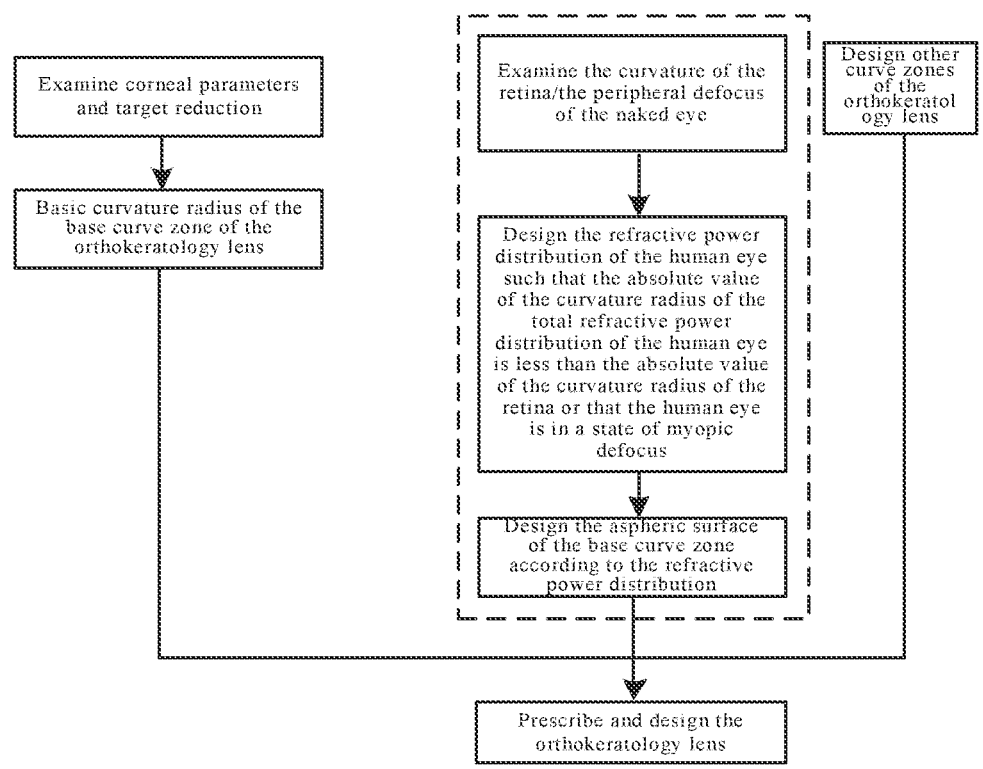
FIG. 11 is a flow diagram of Example 4 of the present invention.
Figure 12:
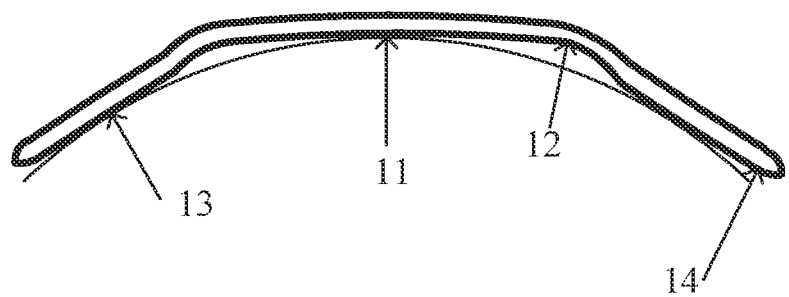
FIG. 12 is a schematic diagram of a longitudinal central section of an existing orthokeratology lens having an inner surface designed as four curve zones.
Figure 13:
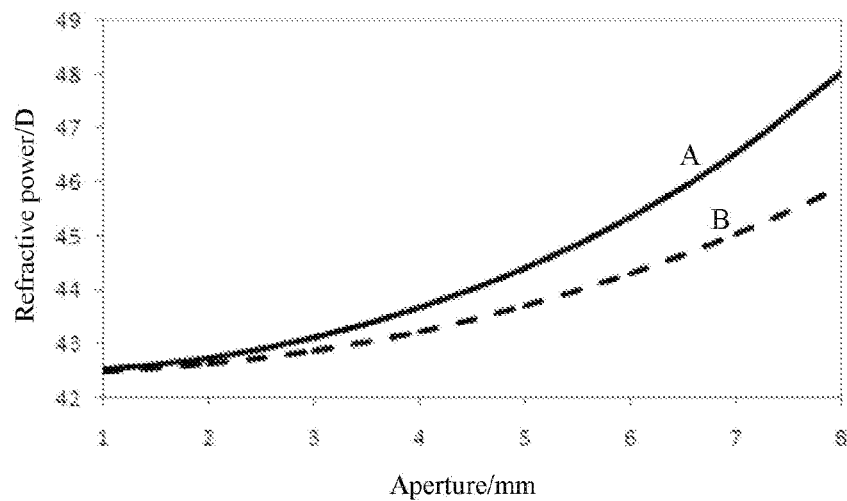
FIG. 13 is a schematic diagram of the refractive power distribution of an existing spherical cornea having a refractive power of 42.25D and an aspheric cornea having an aspheric coefficient Q value of −0.25 and a refractive power of 42.25D at different apertures.

As shown in FIG. 11, in this example, the basic design method of the orthokeratology lens is the same as the existing method, but the surface shape of the base curve zone is determined by the curvature of the retina. The refractive power distribution required by the retina of the human eye is calculated according to the curvature of the retina to ensure that the trend of increase of the refractive power of the human eye along with the increase of the aperture is greater than the curvature of the retina to form hyperopic peripheral defocus, thereby preventing increase of the axial length of the human eye and controlling myopia growth. The surface shape of the inner surface (base curve zone) of the orthokeratology lens is designed according to the distribution of refractive power of the human eye. Since the principle of the orthokeratology lens is that after it is worn on the human eye, the shape of the cornea changes into the shape of the base curve zone of the orthokeratology lens. Therefore, the surface shape of the base curve zone of the orthokeratology lens is the surface shape of the cornea realizing the optical function.

Calculation of the refractive power distribution required by the retina of the human eye according to the curvature of the retina uses the method for preparing an aspheric vision correction lens with controllable peripheral defocus of the present invention. It comprises the steps of:
(1) calculating and determining the conditions required for the formation of myopic defocus of a human eye by examining the shape of the retina of the human eye, the amount of peripheral defocus of the naked human eye or the amount of peripheral defocus of the human eye with a lens;
(2) formulating a plan of distribution of the refractive power of the vision correction lens varying with the aperture, according to the conditions obtained for myopic defocus; and
(3) manufacturing a vision correction lens according to the obtained plan of distribution of the refractive power of the vision correction lens such that after the refractive power of the vision correction lens is added to the human eye, the distribution of the refractive power of the entire eye on the retina is greater in the peripheral region of the retina than in the central region, and falls in front of the retina, to form myopic defocus.

The rest of the contents are the same as above, so it is not repeated here.

Example 5

In this example, the vision correction lens is an intraocular lens.

An intraocular lens mainly refers to a phakic intraocular lens (PIOL) for myopia refraction. PIOL is a negative-power lens implanted surgically between the cornea and lens of the human eye to correct refractive error of the human eye.

Intraocular lenses are divided into the anterior chamber type and the posterior chamber type according to the implantation position. The posterior surface of the anterior chamber type PIOL is generally relatively flat and the anterior surface plays a major role in refraction. The anterior surface of the posterior chamber type PIOL is generally relatively flat, and the posterior surface plays a major role in refraction. They represent two extreme and typical directions of design of negative lenses.

Likewise, the method for preparing an aspheric vision correction lens with controllable peripheral defocus of the present invention comprises the steps of:
(1) calculating and determining the conditions required for the formation of myopic defocus of a human eye by examining the shape of the retina of the human eye, the amount of peripheral defocus of the naked human eye or the amount of peripheral defocus of the human eye with a lens;
(2) formulating a plan of distribution of the refractive power of the vision correction lens varying with the aperture, according to the conditions obtained for myopic defocus; and
(3) manufacturing a vision correction lens according to the obtained plan of distribution of the refractive power of the vision correction lens such that after the refractive power of the vision correction lens is added to the human eye, the distribution of the refractive power of the entire eye on the retina is greater in the peripheral region of the retina than in the central region, and falls in front of the retina, to form myopic defocus.

Through aspheric surface design, an aspheric surface is used to control the surface shape and curvature radius of the optical zone of the lens, such that the radius of curvature changes uniformly at different apertures, the refractive power in the periphery is greater than in the center, and the refractive power distribution has a distribution state of uniform change and hyperopic peripheral defocus, to control myopia growth of the myopic patient.

It will be appreciated by those skilled in the art of lens that the object of the present invention may also be achieved using different combinations of aspheric coefficients in the aspheric surface formula.

On the basis of the design concept of the present invention, those skilled in the art may also conceive achieving hyperopic peripheral defocus of the human eye using the peripheral defocus control idea and diagnosis and treatment method contrary to those in the present invention, so as to treat hyperopia by actively facilitating increase of the axial length of the human eye.

Figure 14:
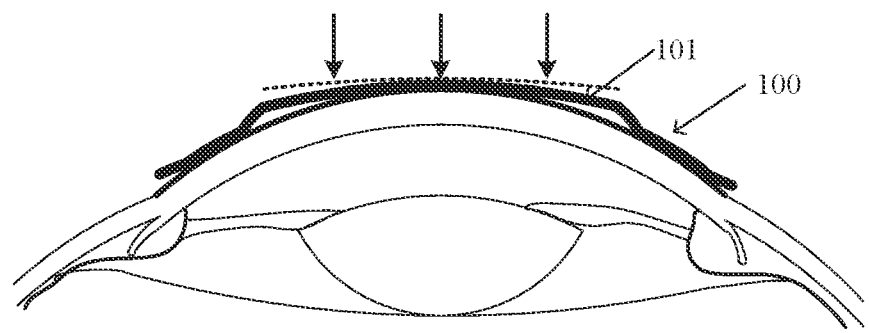
FIG. 14 is a schematic diagram of the structure of an orthokeratology lens of the present invention.
Figure 15:
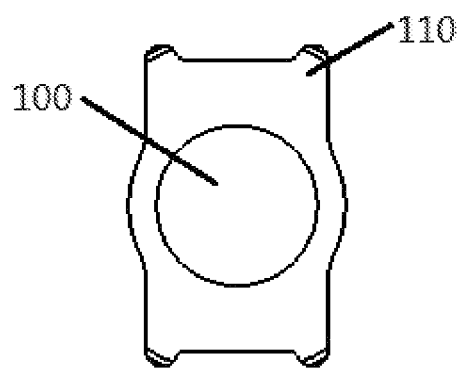
FIG. 15 is a schematic diagram of the structure of an intraocular lens of the present invention.
Figure 16:
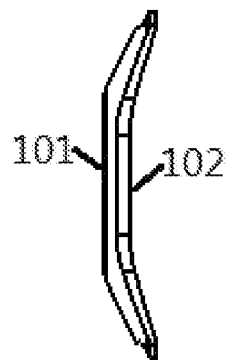
FIG. 16 is a side view of FIG. 15.
Figure 17:
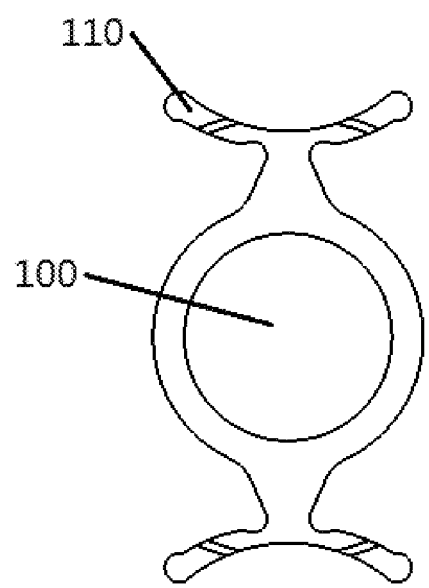
FIG. 17 is a schematic diagram of the structure of another intraocular lens of the present invention.
Figure 18:
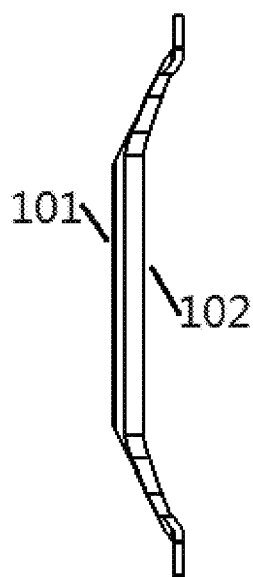
FIG. 18 is a side view of FIG. 17.

As shown in FIG. 14, an orthokeratology lens according to one aspect of the present invention comprises a lens 100. The base curve zone 101 (the optical zone of the surface in contract with the cornea) of the lens 100 is an aspheric surface. The absolute value of the equivalent radius of curvature in the periphery of the base curve zone 101 of the lens 100 is less than the absolute value of the radius of curvature in the center of the base curve zone 101 of the lens 100.

As shown in FIG. 3, the expression of the aspheric surface of the base curve zone 101 of the lens 100 is:

$$Z(y) = \frac{cy^2}{1+\sqrt{1-(1+Q)c^2y^2}} + \sum_{i=2}^{5} A_{2i} \cdot y^{2i}$$

wherein c is the reciprocal of the radius of curvature of the base spherical surface of the optical portion, y is the vertical distance from any point on the curve to the abscissa axis (Z), Q is aspheric coefficient, $A_{2i}$ is aspheric high-order term coefficient, and the aspheric surface is obtained from the aspheric surface curve through rotationally symmetric variation about the abscissa axis (Z).

As shown in FIG. 4, the shape of the aspheric surface of the base curve zone 101 of the lens 100 is defined by the scale factor η of equivalent radii of curvature. The scale factor η of equivalent radii of curvature of the aspheric surface is less than 1.

Scale factor η is the ratio of r of the lens at different diameters $d_m$ and $d_n$, wherein m>n, $$\eta_{mn} = \frac{r_m}{r_n};$$

For a spherical surface, η=1; for an aspheric surface flatter in the periphery than in the center, η>1; and for an aspheric surface steeper in the periphery than in the center, η<1.

The radius of curvature of an aspheric surface cannot be represented by the radius of curvature of a conventional spherical surface, but by an equivalent radius of curvature. The equivalent radius of curvature of the base curve zone 101 of the lens 100 is calculated in the following way, $$r_m = \frac{\left(\frac{d_m}{2}\right)^2 + h_m^2}{2h_m} = \frac{(d_m)^2 + 4h_m^2}{8h_m}$$

wherein $d_m$ is the measured aperture; M is the point at the aperture $d_m$; $h_m$ is the sagittal height of point M, i.e., the difference in height between point M and the vertex of the aspheric surface; and $r_m$ is the equivalent radius of curvature at point M.

Preferably, the scale factor $\eta_{53}$ of the equivalent radii of curvature of the aspheric surface of the base curve zone 101 of the lens 100 at the 5 mm aperture and the 3 mm aperture is greater than or equal to 0.67 and less than 1.

More preferably, the scale factor $\eta_{53}$ of the equivalent radii of curvature of the aspheric surface of the base curve zone 101 of the lens 100 at the 5 mm aperture and the 3 mm aperture is greater than or equal to 0.67 and less than or equal to 0.998.

Still more preferably, the scale factor $\eta_{53}$ of the equivalent radii of curvature of the aspheric surface of the base curve zone 101 of the lens 100 at the 5 mm aperture and the 3 mm aperture is greater than or equal to 0.67 and less than or equal to 0.991.

For specific examples of the present invention, please see Table 3 and Table 4, in which Q, A4, A6, and A8 are aspheric coefficients; $\eta_{53}$ is the scale factor of the equivalent radii of curvature of the lens at the 5 mm aperture and the 3 mm aperture.

TABLE 3

Embodiments of Surface Shape of Base Curve Zone of Orthokeratology Lens

| Radius of curvature | Q | $\eta_{53}$ | Radius of curvature | Q | $\eta_{53}$ |
|---|---|---|---|---|---|
| 9.643 | 0.2 | 0.998 | 5.000 | 2.5 | 0.820 |
| 9.643 | 0.5 | 0.994 | 10.000 | 5.0 | 0.940 |
| 9.643 | 1.0 | 0.989 | 7.000 | 0.5 | 0.989 |
| 6.136 | 0.2 | 0.994 | 7.000 | 3.0 | 0.921 |
| 6.136 | 1.0 | 0.969 | 8.000 | 3.0 | 0.944 |
| 6.136 | 3.0 | 0.885 | 5.000 | 0.2 | 0.991 |
| 6.136 | 5.0 | 0.665 | 5.000 | 0.5 | 0.976 |
| 6.136 | 4.0 | 0.818 | 5.000 | 0.7 | 0.966 |
| 5.000 | 1.0 | 0.949 | 5.000 | 2.0 | 0.876 |
| 5.000 | 1.2 | 0.937 | 5.000 | 2.5 | 0.820 |
| 5.000 | 1.5 | 0.917 | 5.000 | 2.9 | 0.741 |

TABLE 4

Embodiments of Surface Shape of Base Curve Zone of Orthokeratology Lens

| Radius of curvature | Q | A4 | A6 | A8 | $\eta_{53}$ |
|---|---|---|---|---|---|
| 5.946 | 9.400E−02 | 1.604E−04 | 1.695E−06 | 2.829E−07 | 0.990 |
| 4.935 | 1.385E−01 | 4.806E−04 | 4.146E−06 | 9.006E−07 | 0.978 |
| 4.934 | 1.385E−01 | 4.702E−04 | 4.087E−06 | 8.892E−07 | 0.978 |
| 4.939 | 1.618E−01 | 6.567E−04 | 1.322E−05 | 8.648E−07 | 0.970 |
| 5.068 | 8.048E−03 | 6.610E−05 | 6.408E−07 | 2.590E−09 | 0.997 |

It would come readily to those skilled in the art that different combinations of aspheric coefficients may be used to achieve an aspheric surface structure the same as that in the present invention.

On the basis of the present invention's concept of controlling myopic growth by myopic peripheral defocus and aspheric surface design of the lens, those skilled in the art may also conceive making, through modified control of the base curve zone of the lens contrary to that in the present invention, the absolute value of the equivalent radius of curvature of the lens at a larger aperture greater than that at a smaller aperture, to achieve hyperopic peripheral defocus of the human eye to thereby treat hyperopia by actively facilitating increase of the axial length of the human eye.

With reference to FIGS. 15, 16, 17 and 18, an intraocular lens according to one aspect of the present invention comprises an optical zone 100 of the lens and a support haptic 110. At least one of the anterior surface 101 or the posterior surface 102 of the optical zone 100 of the lens is aspheric. The aspheric surface makes the absolute value of the equivalent radius of curvature in the periphery of the optical zone 100 of the lens greater than the absolute value of the radius of curvature in the center of the optical zone 100 of the lens.

Figure 19:
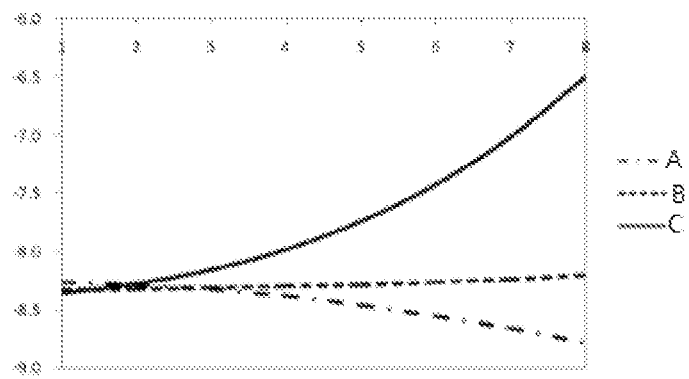
FIG. 19 is a schematic diagram of the refractive power distribution of the present invention and the refractive power distribution of the prior art.

As shown in FIGS. 2 and 19, the lens changes uniformly in the direction of the aperture according to the set refractive power peripheral defocus amount. The refractive power of the lens increases as the aperture increases, and the absolute value of the refractive power decreases as the aperture increases. The refractive power of the lens in the aqueous humor is smaller than or equal to 0D.

In FIG. 19, A is a curve of distribution of the refractive power of a spherical lens, B is a curve of distribution of the refractive power of the existing aspheric lens, and C is a curve of distribution of the refractive power of an intraocular lens of the present invention.

Figure 20:
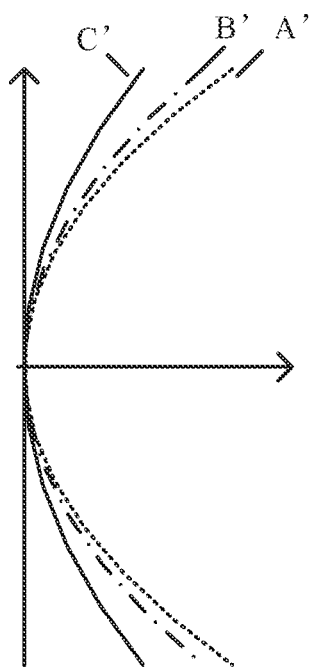
FIG. 20 is a schematic diagram of surface shapes of an aspheric surface of the present invention and an aspheric surface of the prior art.

With reference to FIGS. 3 and 20, the expression of the aspheric surface of the optical zone 100 of the lens is:

$$Z(y) = \frac{cy^2}{1+\sqrt{1-(1+Q)c^2y^2}} + \sum_{i=2}^{5} A_{2i} \cdot y^{2i}$$

wherein c is the reciprocal of the radius of curvature of the base spherical surface of the optical portion, y is the vertical distance from any point on the curve to the abscissa axis (Z), Q is aspheric coefficient, $A_{2i}$ is aspheric high-order term coefficient, and the aspheric surface is obtained from the aspheric surface curve through rotationally symmetric variation about the abscissa axis (Z).

In FIG. 20, A' is a spherical surface base curve, B' is an existing aspheric surface base curve, and C' is an aspheric surface base curve of the present invention.

As shown in FIG. 4, the shape of the aspheric surface of the optical zone 100 of the lens is defined by the scale factor η of equivalent radii of curvature. The scale factor η of equivalent radii of curvature of the aspheric surface is greater than 1.

Scale factor η is the ratio of r of the lens at different apertures $d_m$ and $d_n$, wherein m>n, $$\eta_{mn} = \frac{r_m}{r_n};$$

wherein $d_m$ is the measured aperture; M is the point at the aperture $d_m$; $h_m$ is the sagittal height of point M, i.e., the difference in height between point M and the vertex of the aspheric surface; and $r_m$ is the equivalent radius of curvature at point M.

Preferably, the scale factor $\eta_{43}$ of the equivalent radii of curvature of the aspheric surface of the optical zone of the lens at the 4 mm aperture and the 3 mm aperture is greater than or equal to 1.005.

Preferably, the scale factor $\eta_{43}$ of the equivalent radii of curvature of the aspheric surface of the optical zone of the lens at the 4 mm aperture and the 3 mm aperture is greater than or equal to 1.002 and less than or equal to 1.09.

Preferably, the scale factor $\eta_{43}$ of the equivalent radii of curvature of the aspheric surface of the optical zone of the lens at the 4 mm aperture and the 3 mm aperture is greater than or equal to 1.01 and less than or equal to 1.09.

For several examples of the present invention, please see Table 5. In the table, for the examples involving parameters Rp, Qp, A4, A6 and A8, the aspheric surface is on the posterior surface of the lens, wherein Rp is the radius of curvature of the base spherical surface of the posterior surface, and Qp, A4, A6, A8 are aspheric coefficients. For the examples involving parameters Ra, Qa, A4, A6 and A8, the aspheric surface is on the anterior surface of the lens, wherein Ra is the radius of curvature of the base spherical surface of the anterior surface, and Qa, A4, A6, A8 are aspheric coefficients. $\eta_{43}$ is the scale factor of the equivalent radii of curvature of the lens at the 4 mm aperture and the 3 mm aperture.

TABLE 5

| Examples | | | | | | |
| --- | --- | --- | --- | --- | --- | --- |
| Refractive index | Rp | Qp | A4 | A6 | A8 | $\eta_{43}$ |
| 1.45 | 5.516 | −0.218 | −6.089E−04 | −4.574E−04 | 3.574E−05 | 1.048 |
| 1.48 | 6.838 | −3.263 | −5.330E−04 | −1.525E−06 | 6.005E−08 | 1.041 |
| 1.50 | 7.811 | −3.176 | −5.774E−04 | 1.016E−06 | −1.214E−08 | 1.038 |
| 1.55 | 10.700 | −3.263 | −5.330E−04 | −1.525E−06 | 6.005E−08 | 1.034 |
| 1.60 | 13.200 | −3.263 | −5.330E−04 | −1.525E−06 | 6.005E−08 | 1.035 |
| 1.70 | 18.200 | −3.263 | −5.330E−04 | −1.525E−06 | 6.005E−08 | 1.042 |
| 1.45 | 5.700 | −5.000 | 0 | 0 | 0 | 1.053 |
| 1.45 | 5.700 | −10.000 | 0 | 0 | 0 | 1.086 |
| 1.45 | 5.583 | −0.302 | −6.258E−04 | −5.129E−06 | −1.221E−07 | 1.016 |
| 1.50 | 8.116 | −0.525 | −1.65E−04 | −9.82E−07 | 1.96E−08 | 1.008 |
| 1.55 | 10.634 | −0.530 | −7.84E−05 | −6.75E−07 | 1.93E−08 | 1.005 |
| 1.70 | 18.170 | −0.739 | −7.92E−06 | −4.60E−07 | 1.44E−08 | 1.002 |
| Refractive index | Ra | Qa | A4 | A6 | A8 | $\eta_{43}$ |
| 1.45 | −5.670 | 2.891 | −4.209E−05 | 1.460E−03 | −1.193E−04 | 1.037 |

For a spherical surface, η=1; for an aspheric surface flatter in the periphery than in the center, η>1; and for an aspheric surface steeper in the periphery than in the center, η<1.

The equivalent radius of curvature of the optical zone 100 of the lens is calculated in the following way, $$r_m = \frac{\left(\frac{d_m}{2}\right)^2 + h_m^2}{2h_m} = \frac{(d_m)^2 + 4h_m^2}{8h_m}$$

In light of the object of the present invention, the absolute value of the equivalent radius of curvature of the aspheric surface of the optical zone 100 of the lens at a larger aperture is greater than that at a smaller aperture. The aspheric surface may be located on either of the anterior surface and the posterior surface, or both surfaces are aspheric surfaces.

It would come to those skilled in the art that the object of the present invention may also be achieved by using different combinations of the aspheric coefficients in the aspheric surface formula, and that the shape of the support haptics 110 of the lens may be of any shape that can perform the same function.

On the basis of the present invention's concept of controlling myopic growth by myopic peripheral defocus and aspheric surface design of the lens, those skilled in the art may also conceive making, through contrary modified control of the lens, the absolute value of the refractive power of the lens at a larger aperture greater than that at a smaller aperture, to achieve hyperopic peripheral defocus of the human eye to thereby treat hyperopia by actively facilitating increase of the axial length of the human eye.

The basic principles, main features and advantages of the present invention have been shown and described above. It should be understood by those skilled in the art that the present invention is not limited to the above embodiments, and the above embodiments and description only illustrate the principles of the present invention. Without departing from the spirit and scope of the present invention, the present invention will also have various changes and modifications which fall within the scope of protection of the present invention. The scope of protection of the present invention is defined by the appended claims and the equivalents thereof.

That which is claimed is:

1. A vision correction lens, the vision correction lens having an optical zone, at least one of a convex surface or a concave surface of the optical zone of the lens is aspheric; when the convex surface of the optical zone of the lens is aspheric, an absolute value of an equivalent radius of curvature of the periphery of the optical zone of the lens is smaller than an absolute value of an equivalent radius of curvature of the center of the optical zone of the lens; and when the concave surface of the optical zone of the lens is aspheric, an absolute value of the equivalent radius of curvature of the periphery of the optical zone of the lens is greater than an absolute value of the radius of curvature of the center of the optical zone of the lens, wherein the equivalent radius of curvature is described by:

$$r = \frac{\left(\frac{d}{2}\right)^2 + h^2}{2h} = \frac{d^2 + 4h^2}{8h},$$

wherein r is the equivalent radius of curvature at a diameter, d is the measured aperture at the diameter, and h is the sagittal height of a point of the aspheric surface at the aperture d, i.e., the difference in height between the point and the vertex of the aspheric surface.

2. The vision correction lens according to claim 1, characterized in that the vision correction lens is a correction lens worn outside the eye.

3. The vision correction lens according to claim 2, characterized in that a shape of the aspheric surface of the optical zone of the lens is defined by a scale factor n of equivalent radii of curvature the scale factor η being a ratio of equivalent radii of curvature of the aspheric surface of the optical zone at a first diameter and at a second diameter, wherein the first diameter is greater than the second diameter, $$\eta = \frac{r_m}{r_n},$$

wherein $r_m$ is the equivalent radius of curvature at the first diameter, and $r_n$ is the equivalent radius of curvature at the second diameter, the equivalent radius of curvature of the aspheric surface of the optical zone of the lens is calculated in the following way:

$$r_m = \frac{\left(\frac{d_m}{2}\right)^2 + h_m^2}{2h_m} = \frac{(d_m)^2 + 4h_m^2}{8h_m},$$

wherein $d_m$ is the measured aperture at the first diameter, and $h_m$ is the sagittal height of at first point of the aspheric surface at the aperture $d_m$, i.e., the difference in height between the first point and the vertex of the aspheric surface, $$r_n = \frac{\left(\frac{d_n}{2}\right)^2 + h_n^2}{2h_n} = \frac{(d_n)^2 + 4h_n^2}{8h_n},$$

wherein $d_n$ is the measured aperture at the second diameter, and $h_n$ is the sagittal height of a second point of the aspheric surface at the aperture $d_n$, i.e., the difference in height between the second point and the vertex of the aspheric surface;

wherein when the concave surface of the optical zone of the lens is an aspheric surface, the scale factor η of the equivalent radii of curvature of the aspheric surface is greater than 1, and when the convex surface of the optical zone of the lens is an aspheric surface, the scale factor η of the equivalent radii of curvature of the aspheric surface is less than 1.

4. The vision correction lens according to claim 3, characterized in that when the concave surface of the optical zone of the lens is an aspheric surface, the scale factor $η_{53}$ of the equivalent radii of curvature of the aspheric surface at a 5 mm aperture and a 3 mm aperture being greater than or equal to 1.002 and less than or equal to 1.086; when the convex surface of the optical zone of the lens is an aspheric surface, the scale factor $η_{53}$ of the equivalent radii of curvature of the aspheric surface at the 5 mm aperture and the 3 mm aperture being greater than or equal to 0.682 and less than or equal to 0.986.

5. The vision correction lens according to claim 2, characterized in that the correction lens worn outside the eye is a contact lens or a frame glasses.

6. The vision correction lens according to claim 2, characterized in that the refractive power of the lens in the air is less than or equal to 0D; the refractive power of the lens increases radially as the aperture increases, and the absolute value of the refractive power of the lens decreases as the aperture increases.

7. The vision correction lens according to claim 6, characterized in that the difference between the refractive power of the lens at the 5 mm aperture and the refractive power of the lens at the 3 mm aperture $ΔD_{53}$ is greater than or equal to 0.005D.

8. The vision correction lens according to claim 7, characterized in that the difference between the refractive power of the lens at 5 mm aperture and the refractive power of the lens at the 3 mm aperture $ΔD_{53}$ is greater than or equal to 0.005D and less than or equal to 8.849D.

9. The vision correction lens according to claim 1, characterized in that the vision correction lens is an intraocular lens, wherein at least one of an anterior surface or a posterior surface of the optical zone of the lens is an aspheric surface; the shape of the aspheric surface of the optical zone of the lens is defined by a scale factor η of equivalent radii of curvature, the scale factor η of the equivalent radii of curvature of the aspheric surface is greater than 1;

the scale factor η being a ratio of equivalent radii of curvature of the aspheric surface of the optical zone at a first diameter and at a second diameter, wherein the first diameter is greater than the second diameter, $$\eta = \frac{r_m}{r_n},$$

wherein $r_m$ is the equivalent radius of curvature at the first diameter, and $r_n$ is the equivalent radius of curvature at the second diameter, the equivalent radius of curvature of the optical zone of the lens is calculated in the following way:

$$r_m = \frac{\left(\frac{d_m}{2}\right)^2 + h_m^2}{2h_m} = \frac{(d_m)^2 + 4h_m^2}{8h_m},$$

wherein $d_m$ is the measured aperture at the first diameter; and $h_m$ is the sagittal height of a first point of the aspheric surface at the aperture $d_m$, i.e., the difference in height between the first point and the vertex of the aspheric surface, $$r_n = \frac{\left(\frac{d_n}{2}\right)^2 + h_n^2}{2h_n} = \frac{(d_n)^2 + 4h_n^2}{8h_n},$$

wherein $d_n$ is the measured aperture at the second diameter, and $h_n$ is the sagittal height of a second point of the aspheric surface at the aperture $d_n$, i.e., the difference in height between the second point and the vertex of the aspheric surface.

10. The vision correction lens according to claim 9, characterized in that the scale factor $\eta_{43}$ of the equivalent radii of curvature of the aspheric surface of the optical zone of the lens at a 4 mm aperture and a 3 mm aperture is greater than or equal to 1.002 and less than or equal to 1.09.

11. The vision correction lens according to claim 9, characterized in that the scale factor 143 of the equivalent radii of curvature of the aspheric surface of the optical zone of the lens at a 4 mm aperture and a 3 mm aperture is greater than or equal to 1.005.

12. The vision correction lens according to claim 9, characterized in that the intraocular lens is a phakic intraocular lens.

13. The vision correction lens according to claim 1, wherein the aspheric surface is expressed by:

$$Z(y) = \frac{cy^2}{1 + \sqrt{1-(1+Q)c^2y^2}} + \sum_{i=2}^{5} A_{2i} \cdot y^{2i}$$

wherein $Z(y)$ is an expression of the curve of the aspheric surface of the vision correction lens on the plane YZ, c is the reciprocal of the radius of curvature of a base spherical surface of the optical zone, y is the vertical distance from any point on the curve to the abscissa axis (Z), Q is aspheric coefficient, $A_{2i}$ is aspheric high-order term coefficient, and the points on the aspheric surface are obtained from the curve through rotationally symmetric variation about the abscissa axis (Z), and wherein $A_{2i}$ is not equal to zero.

14. The vision correction lens according to claim 1, wherein the aspheric surface is expressed by:

$$Z(y) = \frac{cy^2}{1 + \sqrt{1-(1+Q)c^2y^2}} + \sum_{i=2}^{5} A_{2i} \cdot y^{2i}$$

wherein $Z(y)$ is an expression of the curve of the aspheric surface of the vision correction lens on the plane YZ, c is the reciprocal of the radius of curvature of a base spherical surface of the optical zone, y is the vertical distance from any point on the curve to the abscissa axis (Z), Q is aspheric coefficient, $A_{2i}$ is aspheric high-order term coefficient, and the points on the aspheric surface are obtained from the curve through rotationally symmetric variation about the abscissa axis (Z), and wherein Q is not equal to zero, and $A_{2i}$ is equal to zero.

* * * * *

UNITED STATES PATENT AND TRADEMARK OFFICE
CERTIFICATE OF CORRECTION

PATENT NO. : 12,313,918 B2
APPLICATION NO. : 17/834139
DATED : May 27, 2025
INVENTOR(S) : Wang et al.

Page 1 of 1

It is certified that error appears in the above-identified patent and that said Letters Patent is hereby corrected as shown below:

In the Specification

Column 15, Line 66: Please correct "ΔD53" to read --$\Delta D_{53}$--

Column 17, Line 14: Please correct "ΔD53" to read --$\Delta D_{53}$--

In the Claims

Column 27, Line 57, Claim 3: Please correct "factor n" to read --factor η--

Column 30, Line 4, Claim 11: Please correct "factor 143" to read --factor $\eta_{43}$--

Signed and Sealed this
Sixteenth Day of September, 2025

Coke Morgan Stewart
*Acting Director of the United States Patent and Trademark Office*